(12) United States Patent
Wang et al.

(10) Patent No.: US 11,246,961 B2
(45) Date of Patent: Feb. 15, 2022

(54) ENGINEERED SCAFFOLDS FOR VASCULARIZED TISSUE REPAIR

(71) Applicant: The Regents of the University of California, Oakland, CA (US)

(72) Inventors: Aijun Wang, Sacramento, CA (US); Kit Lam, Davis, CA (US)

(73) Assignee: The Regents of the University of California, Oakland, CA (US)

(*) Notice: Subject to any disclaimer, the term of this patent is extended or adjusted under 35 U.S.C. 154(b) by 11 days.

(21) Appl. No.: 16/124,505

(22) Filed: Sep. 7, 2018

(65) Prior Publication Data

US 2019/0247539 A1    Aug. 15, 2019

Related U.S. Application Data

(63) Continuation of application No. PCT/US2017/021855, filed on Mar. 10, 2017.

(60) Provisional application No. 62/307,050, filed on Mar. 11, 2016.

(51) Int. Cl.

| A61L 27/22 | (2006.01) |
|---|---|
| C07K 14/78 | (2006.01) |
| A61L 27/16 | (2006.01) |
| A61L 27/18 | (2006.01) |
| A61L 27/38 | (2006.01) |
| C07K 7/64 | (2006.01) |
| C08L 27/18 | (2006.01) |
| C08L 67/04 | (2006.01) |
| A61K 38/00 | (2006.01) |

(52) U.S. Cl.
CPC .............. *A61L 27/22* (2013.01); *A61L 27/16* (2013.01); *A61L 27/18* (2013.01); *A61L 27/3821* (2013.01); *C07K 7/64* (2013.01); *C07K 14/78* (2013.01); *C08L 27/18* (2013.01); *C08L 67/04* (2013.01); *A61K 38/00* (2013.01); *C08L 2203/02* (2013.01)

(58) Field of Classification Search
None
See application file for complete search history.

(56) References Cited

U.S. PATENT DOCUMENTS

| 8,956,643 B2 | 2/2015 | Han et al. | |
| 9,073,974 B2 * | 7/2015 | Lam | C07K 7/64 |
| 2004/0044403 A1 | 3/2004 | Bischoff et al. | |
| 2011/0052710 A1 | 3/2011 | Lillard et al. | |
| 2011/0306722 A1 | 12/2011 | Lellouche et al. | |
| 2012/0322145 A1 | 12/2012 | Onofiok et al. | |
| 2013/0172270 A1 * | 7/2013 | Lam | C07K 7/64 |
| | | | 514/21.1 |

FOREIGN PATENT DOCUMENTS

| WO | 1996/020002 A1 | 7/1996 |
| WO | 2011/079015 A1 | 6/2011 |
| WO | 2017/156427 A3 | 9/2017 |

OTHER PUBLICATIONS

Zhen Yang et al., Shanghai Science and Technology Press, the first version, Jul. 2004, pp. 673-675. (Machine Translation of Section 1 and Section 5).
Hao et al., "Discovery and Characterization of a Potent and Specific Peptide Ligand Targeting Endothelial Progenitor Cells and Endothelial Cells for Tissue Regeneration," ACS Chem Biol., Apr. 21, 2017, vol. 12, No. 4, pp. 1075-1086.
Liu et al., "Design, Synthesis, and Application of OB2C Combinatorial Peptide and Peptidomimetic Libraries," Methods Mal Biol., 2015, vol. 1248, pp. 3-22.
Tan et al., "Surface Engineering and Patterning Using Parylene for Biological Applications", Materials, vol. 3, 2010, pp. 1803-1832.
Wang et al., "Optimization of RGD-Containing Cyclic Peptides against αvβ3 Integrin," Mol Cancer Ther., Feb. 2016, vol. 15, No. 2, pp. 232-240.
European Application No. 17764206.3, Extended European Search Report dated Jul. 24, 2019, 9 pages.
International Application No. PCT/US2017/021855, Invitation to Pay Additional Fees dated Apr. 13, 2017, 2 pages.

* cited by examiner

*Primary Examiner* — Robert A Wax
*Assistant Examiner* — Randeep Singh
(74) *Attorney, Agent, or Firm* — Kilpatrick Townsend & Stockton LLP

(57) ABSTRACT

The present invention provides scaffolds that include a polymer and a cyclic peptide ligand. The peptide ligand increases the attachment of endothelial cells and/or progenitor cells to the scaffold. The present invention also provides engineered tissues that include the provided scaffolds. The present invention also provides coatings that include a coating polymer and a cyclic peptide ligand. The present invention also provides methods of improving endothelialization and vascularization of endothelial cells and/or progenitor cells for tissue regeneration in a subject and of repairing bone defects in a subject, by implanting a provided scaffold.

24 Claims, 26 Drawing Sheets

Specification includes a Sequence Listing.

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Arg Gly Asp
1

ENGINEERED SCAFFOLDS FOR VASCULARIZED TISSUE REPAIR

CROSS-REFERENCE TO RELATED APPLICATIONS

The present application is a continuation of International Patent Application No. PCT/US2017/021855, filed Mar. 10, 2017, which claims priority to U.S. Provisional Application No. 62/307,050, filed Mar. 11, 2016, the disclosures of which are herein incorporated by reference in their entirety for all purposes.

REFERENCE TO A SEQUENCE LISTING

The Sequence Listing written in file 070772-223010US-110848_SL.txt created on Jul. 16, 2021, 550 bytes, machine format IBM-PC, MS-Windows operating system, is herby incorporated by reference in its entirety for all purposes.

BACKGROUND OF THE INVENTION

During the last few decades, tissue engineering has made considerable progress in the development of tissue substitutes and transplantable organs that maintain, restore, or improve host tissue functions (Langer (2000) *Mol Therapy* 1:12). Local endothelial cells (ECs) and circulating endothelial progenitor cells (EPCs) play vital roles in vascularizing these engineered tissue constructs, affecting the long-term survival and function of neotissue formation (Carmeliet and Jain (2011) *Nature* 473:298; Yoder and Ingram (2009) *Curr Opinion Hematology* 16:269). This vascularization process has been identified as a major challenge and a limiting factor for successful translation of engineered tissue products (Santos and Reis (2010) *Macromol Biosci* 10:12).

Biomaterial-based scaffolds are widely used in tissue engineering applications to provide a structural support for cells that have been either transplanted or recruited in situ, allowing the cells to attach, proliferate and form new vascular network (Gong and Niklason (2006) 16:153; Zhang et al. (2007) *J Cell Mol Med* 11:945). Bioactive motifs present on native extracellular matrices (ECM) are critical in providing cell-binding sites for such cell and tissue adhesion, growth, and function (Frantz et al. (2010) *J Cell Sci* 123: 4195; Hynes (2009) *Science* 326: 1216). Synthetic materials can be precisely designed to mimic the physical structure of ECM via various sophisticated bioengineering approaches, but their applications are limited due to the lack of the bioactive motifs that are present on native ECM. Creating a functional bioactive coating on the synthetic material surface to mimic native ECM could significantly improve the biological functions of artificial scaffolds (Jordan and Chaikof (2007) *J Vascular Surgery* 45:104; Rose et al. (2004) *Biomaterials* 25:5125; Williams (2008) *Biomaterials* 29:2941). Various functional biomolecules and strategies have been used to modify biomaterial-based scaffolds to improve endothelialization and vascularization in the scaffolds (Yoder (2009); He et al. (2005) *Biomaterials* 26:7606; Lee et al. (2012) *Biomaterials* 33:8343; Yu et al. (2012) *Biomaterials* 33: 8062; Zeng et al. (2012) *Biomaterials* 33:473; Zeng et al. (2010) *Biomaterials* 31:1636; Zheng et al. (2012) *Biomaterials* 33:2880). However, most of these biomolecules are limited in translational application due to their unstable structure, non-specific cell-binding affinity, and inability to functionally interact with ECs. Non-specific binding to undesirable ("off-target") cell types, such as platelets (Klinger and Jelkmann (2002) *J Interferon Cytokine Res* 22:913; Stokes and Granger (2012) *J Physiol* 590:1023; Wagner and Burger (2003) *Arteriosclerosis Thrombosis Vascular Biology* 23:2131) and inflammatory cells (Qin (2012) *Atherosclerosis* 221:2; Shi and Palmer (2011) *Nat Rev: Immunol* 11:762), may cause detrimental body responses to implanted scaffolds. Therefore, a potent, stable, bioactive molecule that can interact specifically with EPCs and ECs from various sources is urgently needed for tissue engineering applications.

In the process of vascular development and regeneration, interactions between integrins, a family of heterodimeric receptors present on the cell surface, and their ligands in the ECM play important roles in vascular adhesion, migration, proliferation, survival and differentiation (Francis (2006) *Methods Mol Biol* 330:331; Malinin et al. (2012) *Curr Opinion Hematology* 19:206). Previous reports showed that sixteen integrins are involved in vascular biology, and that eight of them (α1β1, α2β1, α3β1, α4β1, α5β1, α6β1, αvβ3, and αvβ5) are expressed on EPCs and ECs at varying times (Rupp and Little (2001) 89:566; Caiado and Dias (2012) *Fibrogenesis Tissue Repair* 5:4). Thus, ligands that bind to integrins expressed on EPCs and ECs represent good candidates for creating a bioactive surface similar to that of native ECM to improve EPC and EC attachment and vascularization. As an example, the arginine-glycine aspartic acid (RGD) motif is the most common integrin-binding sequence found within many ECM proteins and disintegrins (Curly et al. (1999) *Cell Mol Life Sci* 56:427; D'Souza et al. (1991) *Trends Biochem Sci* 16:246; Jin and Varner (2004) *British J Cancer* 90:561; Ruoslahti and Pierschbacher (1986) *Cell* 44:517; Brooks et al. (1994) *Science* 264:569). However, the RGD motif has been found to lack specificity as different integrins recognize diverse RGD-containing native proteins and peptides (Goodman et al. (2002) 45:1045). Therefore, there is a critical need to identify novel ligands that target specific integrins with high binding specificity and affinity for EPCs and ECs. There is a further need to develop scaffolds and methods that apply these novel ligands, improving the angiogenesis and endothelialization of engineered tissues. The present invention surprisingly addresses these and other needs.

BRIEF SUMMARY OF THE INVENTION

In general, provided herein are compositions and methods for improved angiogenesis and endothelialization. The creation of medical devices or scaffolds with these compositions or methods has novel therapeutic potential for vascular, intravascular, blood contacting, or tissue engineering applications.

One provided scaffold comprises a polymer and a peptide ligand covalently immobilized on the surface of the polymer. The peptide ligand increases the attachment of endothelial cells and/or endothelial progenitor cells to the scaffold, and is a compound of Formula I:

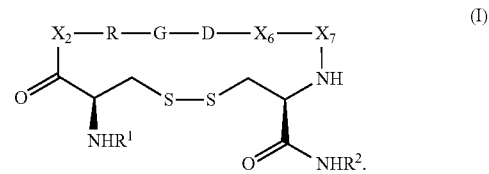

$X_2$, $X_6$, and $X_7$ can each independently be an amino acid, wherein at least one of $X_2$, $X_6$, and $X_7$ is a D-amino acid. $R^1$ of formula I can be H, $C_{1-6}$ alkyl, —C(O)$R^{1a}$, or L-A. $R^{1a}$ can be $C_{1-6}$ alkyl, $C_{1-6}$ heteroalkyl, $C_{1-6}$ alkyl-NH$_2$, $C_{1-6}$ alkyl-C(O)N(H)—$C_{1-6}$ heteroalkyl, cycloalkyl, $C_{1-6}$ alkyl-cycloalkyl, heterocycloalkyl, $C_{1-6}$ alkyl-heterocycloalkyl, aryl, $C_{1-6}$ alkyl-aryl, heteroaryl, or $C_{1-6}$ alkyl-heteroaryl, wherein the cycloalkyl, heterocycloalkyl, heteroaryl and aryl groups can be optionally substituted with a member that can be halogen, —NO$_2$, —OH, —CN, $C_{1-6}$ alkyl, $C_{1-6}$ alkoxy, $C_{1-6}$ haloalkyl, or $C_{1-6}$ haloalkoxy. $R^2$ can be H, $C_{1-6}$ alkyl, or L-A. L is a linker, and A is an active agent.

Also provided is an engineered tissue including a scaffold comprising a polymer and a peptide ligand of Formula I covalently immobilized on the surface of the polymer.

Also provided is a coating including a coating polymer and a peptide ligand of Formula I covalently attached to the coating polymer.

Also provided is a method for improving endothelialization and vascularization of endothelial cells and/or endothelial progenitor cells for tissue regeneration in a subject, the method including implanting a scaffold comprising a polymer and a peptide ligand of Formula I covalently immobilized on the surface of the polymer.

Also provided is a method for repairing a bone defect in a subject, the method including implanting a scaffold comprising a polymer and a peptide ligand of Formula I covalently immobilized on the surface of the polymer. In some embodiments, the bone defect is a calvarial bone defect.

Also provided is a method of coating a surface, the method including functionalizing a coating polymer, and adhering the coating polymer to the surface. The method further includes covalently attaching a peptide ligand of Formula I to the coating polymer.

BRIEF DESCRIPTION OF THE DRAWINGS

FIG. 12 discloses "GRGD" as SEQ ID NO: 1.

DETAILED DESCRIPTION OF THE INVENTION

I. General

Figure 1:
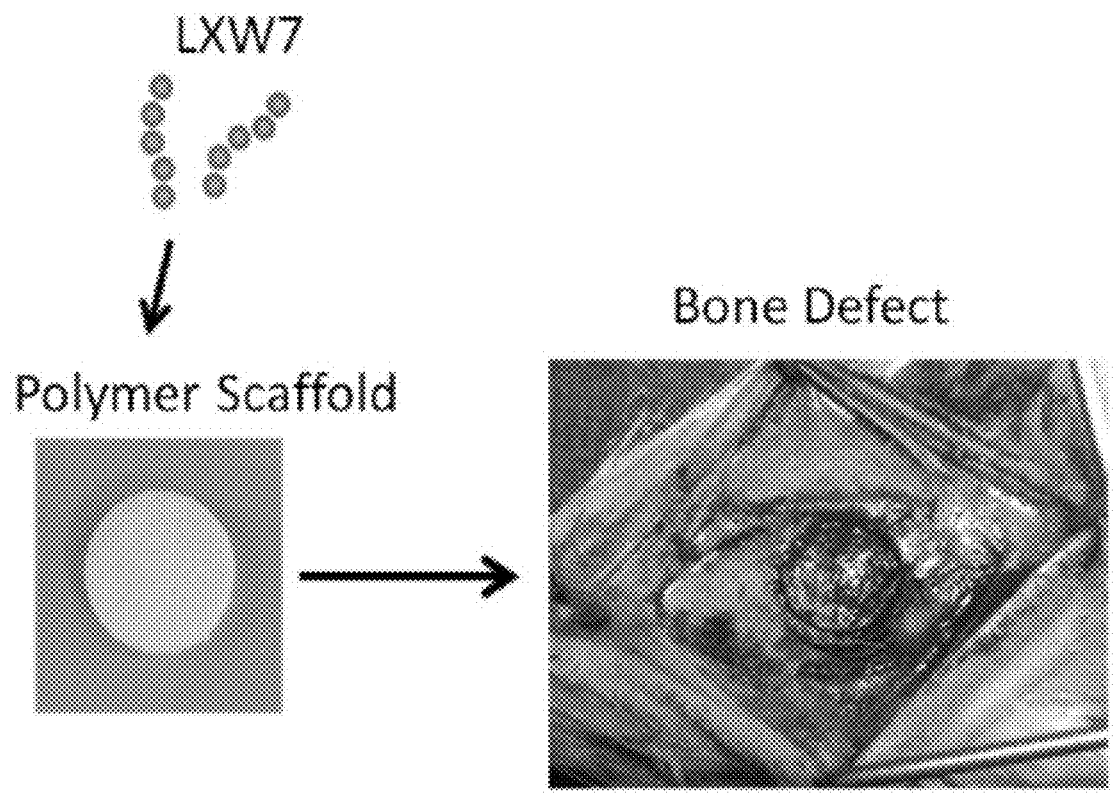
FIG. 1 illustrates an embodiment in which a medical device is created by coating with an integrin ligand and optionally seeding with cells prior to implantation. The medical device can be used to repair critical size calvarial or other bone defects, with the integrin ligand coating functioning to increase the attachment of transplanted cells or the recruitment of endogenous cells to the scaffold.

The present invention provides scaffolds that include a polymer and a cyclic peptide ligand. The peptide ligand increases the attachment of endothelial cells and/or progenitor cells to the scaffold. The present invention also provides engineered tissues that include the provided scaffolds. The present invention also provides methods of improving endothelialization and vascularization of endothelial cells and/or progenitor cells for tissue regeneration in a subject, and of repairing bone defects in a subject, by implanting a provided scaffold.

II. Definitions

The term "scaffold" refers to a matrix that provides a three-dimensional structure suitable for cell culture, tissue engineering, or tissue regeneration. The structure of a scaffold can have, for example, the form of a stent, a shunt, a patch, a graft, or an implant. Scaffolds can be modified to promote cell recruitment, adhesion, or proliferation. Exemplary modifications include, but are not limited to, incorporation of one or more cell adhesion promoters, surface coatings, or functional groups.

The term "amino acid" refers to naturally-occurring α-amino acids and their stereoisomers, as well as unnatural amino acids and their stereoisomers. "Stereoisomers" of amino acids refers to mirror image isomers of the amino acids, such as L-amino acids or D-amino acids. For example, a stereoisomer of a naturally-occurring amino acid refers to the mirror image isomer of the naturally-occurring amino acid, i.e., the D-amino acid.

Amino acids may be referred to herein by either their commonly known three letter symbols or by the one-letter symbols recommended by the IUPAC-IUB Biochemical Nomenclature Commission. For example, an L-amino acid may be represented herein by its commonly known three letter symbol (e.g., Arg for L-arginine) or by an upper-case one-letter amino acid symbol (e.g., R for L-arginine). A D-amino acid may be represented herein by its commonly known three letter symbol with "D" as prefix (e.g., DArg, D-Arg or DArg for D-arginine) or by a lower-case one-letter amino acid symbol (e.g., r for D-arginine).

Amino acids can be characterized by at least one of several properties. For example, amino acids can be basic, acidic,-polar or hydrophobic. Basic amino acids are those having a basic or positively charged side chain at pH values below the pKa, and include, but are not limited to, Lys, Arg, HoArg, Agp, Agb, Dab, Dap and Orn and stereoisomers thereof. Acidic amino acids are those having an acidic or negatively charged side chain at physiological pH, and include, but are not limited to, Asp, Glu, Aad, Bec and stereoisomers thereof. Basic amino acids can generally be referred by the symbol "$X^+$" and acidic amino acids by "$X^-$". Polar amino acids generally refer to those having a polar and uncharged side chain and include, but are not limited to, Asn, Ser, Thr, Gln. Similarly, hydrophobic amino acids generally refer to those having a hydrophobic side chain and include, but are not limited to, Val, Leu, Ile, Met, and Phe. One of skill in the art will appreciate that other basic and acidic amino acids are known in the art.

With respect to amino acid sequences, one of skill in the art will recognize that individual substitutions, additions, or deletions to a peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. The chemically similar amino acid includes, without limitation, a naturally-occurring amino acid such as an L-amino acid, a stereoisomer of a naturally occurring amino acid such as a D-amino acid, and an unnatural amino acid such as an amino acid analog, amino acid mimetic, synthetic amino acid, N-substituted glycine, and N-methyl amino acid.

Conservative substitution tables providing functionally similar amino acids are well known in the art. For example, substitutions may be made wherein an aliphatic amino acid (e.g., G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, e.g., E or D, may be substituted with its uncharged counterpart, e.g., Q or N, respectively; or vice versa. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins,* 1984)

The term "peptide" refers to a compound made up of a single chain of D or L amino acids or a mixture of D and L amino acids joined by peptide bonds. Generally, peptides are about 2 to about 50 amino acids in length. Preferably, the peptides of the present invention are about 2 to about 25 amino acids in length, more preferably 3 to 20 amino acids in length, and most preferably 3 to 10 amino acids in length.

The term "biopolymer" refers to either a naturally occurring polymer, or a synthetic polymer that is compatible with a biological system or that mimics naturally occurring polymers. For example, and not by way of limitation, biopolymers of the present invention include oligosaccharides, proteins, polyketides, peptoids, hydrogels, poly(glycols) such as poly(ethylene glycol), and polylactates.

The term "ligand" refers to a molecule that selectively binds, covalently or noncovalently, to another specific molecule or to a specific part of a molecule.

The term "bind" includes any physical or chemical attachment or close association, which may be permanent or temporary.

The term "noncovalent interactions" refers to the interaction of two species in close proximity that does not form a covalent bond. Types of noncovalent interactions include, for example, hydrogen bonding, van der Waals interaction, coordination, pi-pi interaction, hydrophobic interactions and hydrophilic interactions.

The term "covalent interaction" refers to the interaction of two species in close proximity that form a covalent bond.

The term "αvβ3 integrin" refers to a receptor of vitronectin. αvβ3 integrin serves as a receptor for a variety of extracellular matrix proteins displaying the arginine-glycine-aspartic acid (RGD) tripeptide sequence. These proteins include vitronectin, fibronectin, fibrinogen, laminin, collagen, Von Willibrand's factor.

The term "subject" refers to animals such as mammals, including, but not limited to, primates (e.g., humans), cows, sheep, goats, horses, dogs, cats, rabbits, rats, mice and the like. In certain embodiments, the subject is a human.

The term "alkyl" refers to a straight or branched, saturated, aliphatic radical having the number of carbon atoms indicated. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but can be divalent, such as when the alkyl group links two moieties together.

The term "alkoxy" refers to an alkyl group having an oxygen atom that connects the alkyl group to the point of attachment. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. For example, the alkoxy groups can be substituted with halogens to form a "halo-alkoxy" group.

As used herein, the term "heteroalkyl" refers to an alkyl group having from 1 to 3 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heteroalkyl can include ethers, thioethers and alkyl-amines.

As used herein, the term "haloalkyl" refers to alkyl as defined above where some or all of the hydrogen atoms are substituted with halogen atoms. Halogen (halo) preferably represents chloro or fluoro, but may also be bromo or iodo. For example, haloalkyl includes trifluoromethyl, flouromethyl, 1,2,3,4,5-pentafluoro-phenyl, etc. The term "perfluoro" defines a compound or radical which has at least two available hydrogens substituted with fluorine. For example, perfluorophenyl refers to 1,2,3,4,5-pentafluorophenyl, perfluoromethane refers to 1,1,1-trifluoromethyl, and perfluoromethoxy refers to 1,1,1-trifluoromethoxy.

As used herein, the term "halo-alkoxy" refers to an alkoxy group having at least one halogen. Halo-alkoxy is as defined for alkoxy where some or all of the hydrogen atoms are substituted with halogen atoms. The alkoxy groups can be substituted with 1, 2, 3, or more halogens. When all the hydrogens are replaced with a halogen, for example by fluorine, the compounds are per-substituted, for example, perfluorinated. Halo-alkoxy includes, but is not limited to, trifluoromethoxy, 2,2,2,-trifluoroethoxy, perfluoroethoxy, etc.

As used herein, the term "halogen" refers to fluorine, chlorine, bromine and iodine.

As used herein, the term "cycloalkyl" refers to a saturated or partially unsaturated, monocyclic, fused bicyclic or bridged polycyclic ring assembly containing from 3 to 12 ring atoms, or the number of atoms indicated Monocyclic rings include, for example, cyclopropyl, cyclobutyl, cyclopentyl, cyclohexyl, and cyclooctyl. Bicyclic and polycyclic rings include, for example, norbornane, decahydronaphthalene and adamantane. For example, $C_{3-8}$cycloalkyl includes cyclopropyl, cyclobutyl, cyclopentyl, cyclohexyl, cyclooctyl, and norbornane.

As used herein, the term "alkyl-cycloalkyl" refers to a radical having an alkyl component and a cycloalkyl component, where the alkyl component links the cycloalkyl component to the point of attachment. The alkyl component is as defined above, except that the alkyl component is at least divalent in order to link to the cycloalkyl component and to the point of attachment. In some instances, the alkyl component can be absent. The cycloalkyl component is as defined within. Examples of alkyl-cycloalkyl include methylene-cyclohexane, among others.

As used herein, the term "heterocycloalkyl" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

As used herein, the term "alkyl-heterocycloalkyl" refers to a radical having an alkyl component and a heterocycloalkyl component, where the alkyl component links the heterocycloalkyl component to the point of attachment. The alkyl component is as defined above, except that the alkyl component is at least divalent in order to link to the heterocycloalkyl component and to the point of attachment. In some instances, the alkyl component can be absent. The heterocycloalkyl component is as defined above. Examples of alkyl-heterocycloalkyl include methylene-piperidinyl, among others.

As used herein, the term "aryl" refers to a monocyclic or fused bicyclic, tricyclic or greater, aromatic ring assembly containing 6 to 16 ring carbon atoms. For example, aryl may be phenyl, benzyl or naphthyl, preferably phenyl. "Arylene"

means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Preferred as aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

Examples of substituted phenyl groups as R are, e.g. 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-phen-yl, 4-(imidazol-1-ylmethyl)-phen-1-yl, 4-(morpholin-1-yl)-phen-1-yl, 4-(morpholin-1-ylmethyl)-phen-1-yl, 4-(2-methoxyethylaminomethyl)-phen-1-yl and 4-(pyrrolidin-1-ylmethyl)-phen-1-yl, 4-(thiophenyl)-phen-1-yl, 4-(3-thiophenyl)-phen-1-yl, 4-(4-methylpiperazin-1-yl)-phen-1-yl, and 4-(piperidinyl)-phenyl and 4-(pyridinyl)-phenyl optionally substituted in the heterocyclic ring.

As used herein, the term "alkyl-aryl" refers to a radical having an alkyl component and an aryl component, where the alkyl component links the aryl component to the point of attachment. The alkyl component is as defined above, except that the alkyl component is at least divalent in order to link to the aryl component and to the point of attachment. In some instances, the alkyl component can be absent. The aryl component is as defined above. Examples of alkyl-aryl groups include, but are not limited to, benzyl.

As used herein, the term "Heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2,4-triazolyl). Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR' R", —N$_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R" and R''' are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

As used herein, the term "alkyl-heteroaryl" refers to a radical having an alkyl component and a heteroaryl component, where the alkyl component links the heteroaryl component to the point of attachment. The alkyl component is as defined above, except that the alkyl component is at least divalent in order to link to the heteroaryl component and to the point of attachment. In some instances, the alkyl component can be absent. The heteroaryl component is as defined within. Examples of alkyl-heteroaryl include methylene-pyridyl, among others.

III. Scaffolds

The present invention provides several scaffolds that promote the attachment of endothelial cells and/or endothelial progenitor cells. The scaffolds include a polymer and a peptide ligand covalently immobilized on the surface of the polymer. The peptide ligand is selected to increase the attachment of endothelial cells and/or endothelial progenitor cells to the scaffold, and is a compound of Formula I:

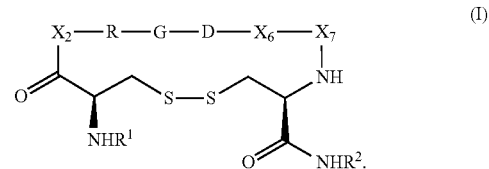

(I)

$X_2$, $X_6$, and $X_7$ can each independently be an amino acid, wherein at least one of $X_2$, $X_6$, and $X_7$ is a D-amino acid. $R^1$ of formula I can be H, $C_{1-6}$ alkyl, —C(O)$R^{1a}$, or L-A. $R^{1a}$ can be $C_{1-6}$ alkyl, $C_{1-6}$ heteroalkyl, $C_{1-6}$ alkyl-NH$_2$, $C_{1-6}$ alkyl-C(O)N(H)—$C_{1-6}$ heteroalkyl, cycloalkyl, $C_{1-6}$ alkyl-cycloalkyl, heterocycloalkyl, $C_{1-6}$ alkyl-heterocycloalkyl, aryl, $C_{1-6}$ alkyl-aryl, heteroaryl, or $C_{1-6}$ alkyl-heteroaryl, wherein the cycloalkyl, heterocycloalkyl, heteroaryl, and aryl groups are optionally substituted with a halogen, —NO$_2$, —OH, —CN, $C_{1-6}$ alkyl, $C_{1-6}$ alkoxy, $C_{1-6}$ haloalkyl, or $C_{1-6}$ haloalkoxy. $R^2$ can be H, $C_{1-6}$ alkyl, or L-A. Radical L is a linker and radical A is an active agent.

The compounds of formula I can include basic amino acids, such as those having a positively charged side chain. Non-limiting examples of basic amino acids are Lys, Arg, HoArg, Agp, Agb, Dab, Dap and Orn, and stereoisomers thereof. The compounds of formula I can also include acidic amino acids, such as those with a negatively charged side chain. Non-limiting examples of acidic amino acids are Asp, Glu, Aad, and Bec, and stereoisomers thereof. Basic amino acids can generally be referred by the symbol "X$^+$" and acidic amino acids by "X⁻". One of skill in the art will appreciate that other basic and acidic amino acids are known in the art.

Amino acids useful in the compounds of the present invention include naturally-occurring amino acids, as well as those amino acids that are later modified, e.g., γ-carboxyglutamate and O-phosphoserine, as well as unnatural amino acids. Naturally-occurring α-amino acids include (shown with the corresponding 3 letter and single letter codes), without limitation, alanine (Ala, A), cysteine (Cys, C), aspartic acid (Asp, D), glutamic acid (Glu, E), phenylalanine (Phe, F), glycine (Gly, G), histidine (His, H), isoleucine (Ile, I), arginine (Arg, R), lysine (Lys, K), leucine (Leu, L), methionine (Met, M), asparagine (Asn, N), proline (Pro, P), glutamine (Gln, Q), serine (Ser, S), threonine (Thr, T), valine (Val, V), tryptophan (Trp, W) and tyrosine (Tyr, Y). Stereoisomers of a naturally-occurring α-amino acids include, without limitation, D-alanine (DAla, a), D-cysteine (DCys, c), D-aspartic acid (DAsp, d), D-glutamic acid (DGlu, e), D-phenylalanine (DPhe, f), D-histidine (DHis, h), D-isoleucine (DIle, i), D-arginine (DArg, r), D-lysine (DLys, k), D-leucine (DLeu, l), D-methionine (DMet, m), D-asparagine (DAsn, n), D-proline (DPro, p), D-glutamine (DGln, q), D-serine (DSer, s), D-threonine (D-Thr, t), D-valine (D-Val, v), D-tryptophan (DTrp, w) and D-tyrosine (DTyr, y).

Unnatural amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" are unnatural amino acids that have the same basic chemical structure as naturally-occurring amino acids, i.e., an α carbon that is bound to a hydrogen, a carboxyl group, an amino group, but have modified R (i.e., side-chain) groups. Suitable unnatural amino acids include, without limitation, α-aminohexanedioic acid (Aad), α-aminobutyric acid (Abu), 3-aminobenzoic acid (3Abz), azetidine-2-carboxylic acid (Aca), 1-aminocyclobutane-1-carboxylic acid (Acb), α-amino-3-chloro-4,5-dihydro-5-isoazoleacetic acid (Acdi), 4-amino-4-carboxy-1,1-dioxo-tetrahydrothiopyran (Acdt), 1-amino-1-cyclohexane carboxylic acid (Ach), 1-aminocyclopentane-1-carboxylic acid (Acp), 1-aminocyclopropane-1-carboxylic acid (Acpc), 4-amino-4-carboxytetrahydropyran (Actp), 8-amino-1,4-dioxaspiro [4.5]decane-8-carboxylic acid (Aecc), (S)-2-amino-4-guanidino-butanoic acid (Agb), allylglycine (Agl), (S)-2-amino-3-guanidino-propanoic acid (Agp), 2-aminoheptanoic acid (Aha), 1-amino-1-(4-hydroxycyclohexyl) carboxylic acid (Ahch), α-aminoisobutyric acid (Aib), 2-aminoindane-2-carboxylic acid (Aic), 1-amino-1-(4-ketocyclohexyl) carboxylic acid (Akch), 2-aminooctanoic acid (Aoa), 2-amino-2-naphthylacetic acid (Ana), 1-amino-1-(3-piperidinyl) carboxylic acid (3Apc), 1-amino-1-(4-piperidinyl) carboxylic acid (4Apc), 2-amino-3-(4-piperidinyl) propionic acid (4App), homoarginine (HoArg), Nα-methyl-arginine ((NMe)Arg), Nα-methyl-aspartic acid ((NMe)Asp), α-aminooctanedioic acid (Asu), (R)-2-amino-3-(2-carboxyethylsulfanyl)propanoic acid (Bec), 4,4'-biphenylalanine (Bipa), (R)-2-amino-3-(carboxymethylsulfanyl)propanoic acid (Bmc), 4-carboxymethoxyphenylalanine (Bmp), 4-benzoylphenylalanine (Bpa), 3-benzothienylalanine (Bta), 5H-thiazolo[3,2-a]pyridine-3-carboxylic acid (Btd), β-t-butyl-alaine (Bua), α-tert-butylglycine (Bug), 4-cyano-2-aminobutyric acid (Cab), cyclobutylalanine (Cba), cyclohexylalanine (Cha), homocyclohexylalanine (HoCha), α-cyclohexylglycine (Chg), citrulline (Cit), homocitrulline (HoCit), cyclopropylalanine (Cpa), cyclopentylglycine (Cpeg), 3-carboxymethyl-1-phenyl-1,3,8-triazaspiro[4,5] decan-4-one (Cptd), homocysteine (HoCys), α,γ-diaminobutyric acid (Dbu), diethylglycine (Deg), 3,3-diphenyl-alanine (Dpa), di-n-propylglycine (Dpg), α,β-diaminopropionic acid (Dap), α, γ-diaminobutyric acid (Dab), 2-furyl-Alanine (Fua), homoarginine (HoArg), hydroxyproline (Hyp), O-benzyl-hydroxyproline (Hyp (Bzl)), homoleucine (HoLeu), 2-Indanylglycine (Ing), methionine sulfoxide (Met(O)), methionine methylsulfonium (Met (S-Me)), 3-(1-naphthyl)alanine (Nal1), 3-(2-naphthyl)alanine (Nal2), 3-(carboxymethylamino)propanoic acid (Nglu), nipecotic acid (Nip), isonipecotic acid (IsoNip), norleucine (Nle), norvaline (Nva), octahydroindole-2-carboxylic acid (Oic), ornithine (Orn), 2-pyridylalanine (2Pal), 3-(3-pyridyl)alanine (3Pal), 3-(4-pyridyl)alanine (4 Pal), penicillamine (Pen), homophenylalanine (HoPhe), Nα-methyl-phenylalanine ((NMe)Phe), 2-chloro-phenylalanine (Phe(2Cl)), α-methyl-phenylalanine ((CαMe)Phe), 3,4-dimethoxy-phenylalanine (Phe(3,4-di OMe)), 4-carboxyphenylalanine (Phe(4COOH)), 4-nitro-phenylalanine (Phe(4-NO₂)), 4-trifluoromethyl-phenylalanine (Phe(4-CF₃)), 4-tert-butyl-phenylalanine (Phe(4-tBu)), 3,4-dichloro-phenylalanine (Phe(3,4-diCl)), phenylglycine (Phg), (2S,5R)-5-phenyl pyrrolidine-2-carboxylic acid (Ppca), propargylglycine (Pra), homoproline (HoPro), β-homoproline (βHoPro), 2-quinoylalanine (2Qal), Nα-methylglycine (Sar), homoserine (HoSer), 3-styryl-alanine (Sta), taurine (Tau), 4-thiazoylalanine (Tha), 3-(2-thienyl)alanine (2Thi), 3-(3-thienyl)alanine (3 Thi), thiazolidine-4-carboxylic acid (Thz), thiazolidine-2-carboxylic acid (Thz(2-COOH)), tetrahydro-isoquinoline-3-carboxylic acid (3Tic), (R)-1,2,3,4-tetrahydroisoquinoline-3-carboxylic acid (Tic), 3,5-dinitrotyrosine (Tyr(3,5di NO₂)), 3-nitrotyrosine (Tyr(3-NO₂)), 3,5-diiodotyrosine (Tyr(diI)), and Nα-methyl-valine ((NMe)-Val), a phenylalanine analog, derivatives of lysine, and stereoisomers thereof (see, Liu and Lam, *Anal. Biochem.*, 295:9-16 (2001)). As such, the unnatural α-amino acids are present either as unnatural L-α-amino acids, unnatural D-α-amino acids, or combinations thereof.

The amino acids can also be categorized as basic, acidic, hydrophobic and/or polar. Some suitable basic amino acids of the invention are Lys, Arg, HoArg, Agp, Agb, Dab, Dap, Orn and stereoisomers thereof. Some suitable acidic amino acids are Asp, Glu, Aad, Bec and stereoisomers thereof. Hydrophobic amino acids include, but are not limited to, Val, Leu, Ile, Met and Phe, and stereoisomers thereof. Polar amino acids include, but are not limited to, Asn, Ser, Gln, Thr, and stereoisomers thereof.

Suitable phenylalanine analogs include, without limitation, homophenylalanine (HoPhe), phenylglycine (Phg), 3,3-diphenylalanine (Dpa), 4-aminophenylalanine (Phe(4-NH₂)), 2-methylphenylalanine (Phe(2-Me)), 3-methylphenylalanine (Phe(3-Me)), 4-methylphenylalanine (Phe(4-Me)), 4-azidophenylalanine (Phe(4-N₃)), 2-fluorophenylalanine (Phe(2-F)), 3-fluorophenylalanine (Phe(3-F)), 4-fluorophenylalanine (Phe(4-F)), 2-chlorophenylalanine (Phe(2-Cl)), 3-chlorophenylalanine (Phe(3-Cl)), 4-chlorophenylalanine (Phe(4-Cl)), 2-bromophenylalanine (Phe(2-Br)), 3-bromophenylalanine (Phe(3-Br)), 4-bromophenylalanine (Phe(4-Br)), 2-iodophenylalanine (Phe(2-I)), 3-iodophenylalanine (Phe(3-I)), 4-iodophenylalanine (Phe(4-I)), 2-trifluoromethylphenylalanine (Phe(2-CF₃)), 3-trifluoromethylphenylalanine (Phe(3-CF₃)), 4-trifluoromethylphenylalanine (Phe(4-CF₃)), 2-methoxyphenylalanine (Phe(2-OMe)), 3-methoxyphenylalanine (Phe(3-OMe)), 2-nitrophenylalanine (Phe(2-NO₂)), 3-nitrophenylalanine (Phe(3-NO₂)), 4-nitrophenylalanine (Phe(4-NO₂)), 2-cyanophenylalanine (Phe(2-CN)), 3-cyanophenylalanine (Phe(3-CN)), 4-cyanophenylalanine (Phe(4-CN)), 3,4-dimethoxyphenylalanine (Phe(3,4-di OMe)), 3,4-difluorophenylalanine (Phe(3,4-di F)), 3,5-difluorophenylalanine (Phe(3,5-di F)), 2,4-dichlorophenylalanine (Phe(2,4-diCl)), 3,4-dichlorophenylalanine (Phe(3,4-diCl)), 4-benzoylphenylalanine (Bpa), 4-carboxyphenylalanine (Phe(4COOH)), 4,4'-biphenylalanine (Bip), 2,3,4,5,6-pentafluorophenylalanine (Phe(F5)), 3,4,5-trifluorophenylalanine (Phe(F3)), 4-chlorophenylglycine (Phg(4-Cl)), 2-chlorophenylglycine (Phg(2-Cl)), 3-chlorophenylglycine (Phg(3-Cl)), 4-bromophenylglycine (Phg(4-Br)), 2-bromophenylglycine (Phg(2-Br)), 3-bromophenylglycine (Phg(3-Br)), 4-ethylphenylalanine (Phe(4-Et)), 4-ethoxyphenylalanine (Phe(4-OEt)), 4-butoxyphenylalanine (Phe(4-OBu)), O-methyltyrosine (Tyr(Me)), O-benzyltyrosine (Tyr(Bzl)), 3,5-dibromotyrosine (Tyr(diBr)), 3,5-diiodotyrosine (Tyr(diI)), homotyrosine (HoTyr), 3-chlorotyrosine (Tyr(3-Cl)), stereoisomers thereof, and combinations thereof.

Suitable derivatives of lysine (Lys), ornithine (Orn) and Dbu, include, without limitation, Lys38, Lys27, Lys73, Lys55, Lys28, Lys72, Lys12, Lys123, Lys63, Lys124, Lys82, Lys31, Lys15, Lys125, Lys43, Lys24, Lys5, Lys4, Lys50, Lys81, Orn38, Orn27, Orn73, Orn55, Orn28, Orn72, Orn12, Orn123, Orn63, Orn124, Orn82, Orn31, Orn15, Orn125, Orn43, Orn24, Orn5, Orn4, Orn50, Orn81, Dbu38, Dbu27, Dbu73, Dbu55, Dbu28, Dbu72, Dbu12, Dbu123, Dbu63, Dbu124, Dbu82, Dbu31, Dbu15, Dbu125, Dbu43, Dbu24, Dbu5, Dbu4, Dbu50, Dbu81, stereoisomers thereof, and combinations thereof. See, Table 1 for a description of the structures for each of the lysine derivatives. Derivatives of Orn and Dbu are similar to the lysine derivatives with corresponding carboxylic acid attached to the side chain of Orn and Dbu, respectively.

Suitable N-methyl amino acids include N-methyl-Ala, N-methyl-Cys, N-methyl-Asp, N-methyl-Glu, N-methyl-Phe, N-methyl-Gly, N-methyl-His, N-methyl-Ile, N-methyl-Arg, N-methyl-Lys, N-methyl-Leu, N-methyl-Met, N-methyl-Asn, N-methyl-Gln, N-methyl-Ser, N-methyl-Thr, N-methyl-Val, N-methyl-Trp, N-methyl-Tyr, N-methyl-Acp, N-methyl-Acb, N-methyl-Acpc, N-methyl-Cit, N-methyl-HoCit, N-methyl-Aad, N-methyl-4-Pal, N-methyl-3-Pal, N-methyl-Pra, N-methyl-Aib, N-methyl-Abu, N-methyl-Nva, N-methyl-Dpr, N-methyl-Dbu, N-methyl-Nle, N-methyl-Nal-2, N-methyl-Nal-1, N-methyl-Cha, N-methyl-Cpa, N-methyl-Hle, N-methyl-HoSer, N-methyl-Har, N-methyl-Hcy, N-methyl-Chg, N-methyl-Bta, N-methyl-2-Thi, N-methyl-3-Thi, N-methyl-Asu, N-methyl-Acdt, N-methyl-Ahch, N-methyl-Akch, N-methyl-Actp, N-methyl-Tyr(3-NO$_2$), N-methyl-Ach, N-methyl-3-Apc, N-methyl-4-Apc, N-methyl-4-App, N-methyl-Tha, N-methyl-Aoa, N-methyl-Aha, N-methyl-Orn, N-methyl-Aca, N-methyl-Agl, N-methyl-Cab, N-methyl-2-Pal, N-methyl-Cba, N-methyl-HoPhe, N-methyl-Phg, N-methyl-Phe(4-NH$_2$), N-methyl-4-Phe(4-Me), N-methyl-Phe(4-F), N-methyl-Phe(4-Cl), N-methyl-Phe(2-Br), N-methyl-Phe(3-Br), N-methyl-Phe(4-Br), N-methyl-Phe(3-CF$_3$), N-methyl-Phe(4-CF$_3$), N-methyl-Phe(4-NO$_2$), N-methyl-Phe(4-CN), N-methyl-Bpa, N-methyl-Phg(4-Cl), N-methyl-Phg(4-Br), N-methyl-Tyr(Me), N-methyl-Lys38, N-methyl-Lys27, N-methyl-Lys73, N-methyl-Lys55, N-methyl-Lys28, N-methyl-Lys72, N-methyl-Lys12, N-methyl-Lys123, N-methyl-Lys63, N-methyl-Lys124, N-methyl-Lys82, N-methyl-Lys31, N-methyl-Lys15, N-methyl-Lys125, N-methyl-Lys43, N-methyl-Lys24, N-methyl-Lys5, N-methyl-Lys4, N-methyl-Lys50, N-methyl-Lys81, N-methyl-Orn38, N-methyl-Orn27, N-methyl-Orn73, N-methyl-Orn55, N-methyl-Orn28, N-methyl-Orn72, N-methyl-Orn12, N-methyl-Orn123, N-methyl-Orn63, N-methyl-Orn124, N-methyl-Orn82, N-methyl-Orn31, N-methyl-Orn15, N-methyl-Orn125, N-methyl-Orn43, N-methyl-Orn24, N-methyl-Orn5, N-methyl-Orn4, N-methyl-Orn50, N-methyl-Orn81, N-methyl-Dbu38, N-methyl-Dbu27, N-methyl-Dbu73, N-methyl-Dbu55, N-methyl-Dbu28, N-methyl-Dbu72, N-methyl-Dbu12, N-methyl-Dbu123, N-methyl-Dbu63, N-methyl-Dbu124, N-methyl-Dbu82, N-methyl-Dbu31, N-methyl-Dbu15, N-methyl-Dbu125, N-methyl-Dbu43, N-methyl-Dbu24, N-methyl-Dbu5, N-methyl-Dbu4, N-methyl-Dbu50, N-methyl-Dbu81, stereoisomers thereof, and combinations thereof.

Amino acid mimetics are chemical compounds that have a structure that is different from the general chemical structure of an amino acid, but that function in a manner similar to a naturally-occurring amino acid. Suitable amino acid mimetics include, without limitation, β-amino acids and γ-amino acids. In β-amino acids, the amino group is bonded to the β-carbon atom of the carboxyl group such that there are two carbon atoms between the amino and carboxyl groups. In γ-amino acids, the amino group is bonded to the γ-carbon atom of the carboxyl group such that there are three carbon atoms between the amino and carboxyl groups. Suitable R groups for β- or γ-amino acids include, but are not limited to, side-chains present in naturally-occurring amino acids and unnatural amino acids.

N-substituted glycines are unnatural amino acids based on glycine, where an amino acid side-chain is attached to the glycine nitrogen atom. Suitable amino acid side-chains (e.g., R groups) include, but are not limited to, side chains present in naturally-occurring amino acids and side-chains present in unnatural amino acids such as amino acid analogs. Examples of N-substituted glycines suitable for use in the present invention include, without limitation, N-(2-aminoethyl)glycine, N-(3-aminopropyl)glycine, N-(2-methoxyethyl)glycine, N-benzylglycine, (S)-N-(1-phenylethyl)glycine, N-cyclohexylmethylglycine, N-(2-phenylethyl)glycine, N-(3-phenylpropyl)glycine, N-(6-aminogalactosyl)glycine, N-(2-(3'-indolylethyl)glycine, N-(2-(p-methoxyphenylethyl))glycine, N-(2-(p-chlorophenylethyl)glycine, and N-[2-(p-hydroxyphenylethyl)]glycine. N-substituted glycine oligomers, referred to herein as "peptoids," have been shown to be protease resistant (Miller et al., *Drug Dev. Res.*, 35:20-32 (1995)). As such, peptoids containing at least one unnatural α-amino acid, D-amino acid, or a combination thereof are within the scope of the present invention.

In still other embodiments, radicals $R^1$ and $R^2$ of formula I can each independently be H, $C_{1-6}$ alkyl or L-A. And radical L can be a linker and radical A can be an active agent.

In still other embodiments, $R^1$ can be acetyl, 3-amino propanoyl, Ebes, isobutyryl, valeryl, cyclohexyl acetyl, 5-bromo-2-furoyl, 3-phenyl propionyl, p-chlorophenyl acetyl, 4-nitrobezoyl, 3,5-dihydroxybeznoyl, 4-(trifluoromethyl)benzoyl, 2-Methylthiazole-4-carbonyl, nicotinyl, 2-naphthoyl, or biphenyl-4-carbonyl.

Linkers useful in the present invention include those possessing one or more different reactive functional groups that allow for covalent attachment of moieties such as a peptide to a chelating agent. The linking moiety possesses two or more different reactive functional groups. In some cases multivalent linkers can be used and multiple RGD peptides of the invention and/or multiple active agents can be linked via the linker. Suitable linkers include, without limitation, those available from Pierce Biotechnology, Inc. (Rockford, Ill.). In preferred embodiments of the present invention, the linker provides a carboxyl group for the attachment of a chelating agent and an amino group for the attachment of a peptide. However, one skilled in the art understands that any reactive functional group can be present on the linker, as long as it is compatible with a functional group on the moiety that is to be covalently attached. As used herein, the term "chelating agent-linker conjugate" refers to a chelating agent covalently attached to a linker. Such chelating agent-linker conjugates can be attached to a peptide via a functional group present on the linker. Some suitable linkers include, but are not limited to, β-alanine, 2,2'-ethylenedioxy bis(ethylamine) monosuccinamide (Ebes) and bis(Ebes)-Lys. Other suitable linkers include those with biotin. Additional linkers can be found in *Bioconjugate Techniques*, Greg T. Hermanson, Academic Press, 2d ed., 2008 (incorporated by reference in its entirety herein).

The linkers can be cleavable linkers designed for cleavage in the presence of particular conditions or in a particular environment. Cleavage of such linkers can, for example, be enhanced or affected by particular pathological signals or by a specific enzyme. Selection of cleavable linkers designed for particular conditions can allow for targeting to specific locations where such conditions exist. Cleavable linkers can be sensitive to, for example, basic pH conditions, acidic pH conditions, protease activity, metalloproteinase activity, or reducing conditions. In some embodiments, the linkers can be cleaved by, for example, disulfide reduction, photocleavage, or protein digestion.

Active agents, A, can be broadly selected. In some embodiments the active agents can be selected from drugs, antimicrobial agents such as antibiotics, vaccines, aptamers, avimers scaffolds based on human A domain scaffolds, diabodies, camelids, shark IgNAR antibodies, fibronectin type III scaffolds with modified specificities, antibodies, antibody fragments, vitamins and cofactors, polysaccharides, carbohydrates, steroids, lipids, fats, proteins, peptides, polypeptides, nucleotides, oligonucleotides, polynucleotides, and nucleic acids (e.g., mRNA, tRNA, snRNA, RNAi, microRNA, DNA, cDNA, antisense constructs, ribozymes, etc, and combinations thereof). In one embodiment, the active agents can be selected from proteins, peptides, polypeptides, soluble or cell-bound, extracellular or intracellular, kinesins, molecular motors, enzymes, extracellular matrix materials and combinations thereof. In another embodiment, active agents can be selected from nucleotides, oligonucleotides, polynucleotides, and nucleic acids (e.g., mRNA, tRNA, snRNA, RNAi, DNA, cDNA, antisense constructs, ribozymes etc and combinations thereof). In another embodiment, active agents can be selected from steroids, lipids, fats and combinations thereof. For example, the active agent can bind to the extracellular matrix, such as when the active agent is hyaluronic acid. Other active agents include diagnostic or therapeutic agents, such as drugs, radiolabels, imaging agents, chemotherapy agents and nanoparticles. In some embodiments, the active agent can be biotin.

Imaging agent refers to a label that is attached to the compounds of the present invention for imaging a tumor, organ, or tissue in a subject. The imaging moiety can be covalently or non-covalently attached to the compound. Examples of imaging moieties suitable for use in the present invention include, without limitation, radionuclides, biotin, fluorophores such as fluorescein, rhodamine, Texas Red, Cy2, Cy3, Cy5 or Cy5.5, Alexa 350, Alexa 405, Alexa 488, Alexa 546, Alexa 555, Alexa 568, Alexa 594, Alexa 633, Alexa 647, Alexa 680, R-phycoerythrin, antibodies, horseradish peroxidase, alkaline phosphatase, derivatives thereof, and mixtures thereof. Exemplary methods for synthesizing the compounds of the present invention as a biotin conjugate or as a DOTA conjugate are provided in Examples 12 and 13, respectively. One skilled in the art will know of other suitable methods for conjugating a particular imaging moiety to the compounds of the present invention.

Radiolabel refers to a nuclide that exhibits radioactivity. A "nuclide" refers to a type of atom specified by its atomic number, atomic mass, and energy state, such as carbon 14 ($^{14}$C). "Radioactivity" refers to the radiation, including alpha particles, beta particles, nucleons, electrons, positrons, neutrinos, and gamma rays, emitted by a radioactive substance. Radionuclides suitable for use in the present invention include, but are not limited to, fluorine 18 ($^{18}$F), phosphorus 32 ($^{32}$P), scandium 47 ($^{47}$Sc), cobalt 55 ($^{55}$Co), copper 60 ($^{60}$Cu), copper 61 ($^{61}$Cu), copper 62 ($^{62}$Cu), copper 64 ($^{64}$Cu), copper 67 ($^{67}$Cu), gallium 66 ($^{66}$Ga), gallium 67 ($^{67}$Ga), gallium 68 ($^{68}$Ga), rubidium 82 ($^{82}$Rb), yttrium 86 ($^{86}$Y), yttrium 87 ($^{87}$Y), yttrium 90 ($^{90}$Y), strontium 89 ($^{89}$Sr), rhodium 105 ($^{105}$Rh) silver 111 ($^{111}$Ag) indium 111 ($^{111}$In), iodine 123 ($^{123}$I), iodine 124 ($^{124}$I) iodine 125 ($^{125}$I) iodine 131 ($^{131}$I), tin 117m ($^{117m}$Sn), technetium 99m ($^{99m}$Tc), promethium 149 ($^{149}$Pm), samarium 153 ($^{153}$Sm), holmium 166 ($^{166}$Ho), lutetium 177 ($^{177}$Lu), rhenium 186 ($^{186}$Re), rhenium 188 ($^{188}$Re), thallium 201 ($^{201}$Tl), astatine 211 ($^{211}$At), and bismuth 212 ($^{212}$Bi). As used herein, the "m" in $^{117m}$Sn and $^{99m}$Tc stands for meta state. Additionally, naturally occurring radioactive elements such as uranium, radium, and thorium, which typically represent mixtures of radioisotopes, are suitable examples of radionuclides. $^{67}$Cu, $^{131}$I, $^{177}$Lu, and $^{186}$Re are beta- and gamma-emitting radionuclides. $^{212}$Bi is an alpha- and beta-emitting radionuclide. $^{211}$At is an alpha-emitting radionuclide. $^{32}$P, $^{47}$Sc, $^{89}$Sr, $^{90}$Y, $^{105}$Rh, $^{111}$Ag, $^{117m}$Sn, $^{149}$Pm, $^{153}$Sm, $^{166}$Ho, and $^{188}$Re are examples of beta-emitting radionuclides. $^{67}$Ga, $^{111}$In, $^{99m}$Tc, and $^{201}$Tl are examples of gamma-emitting radionuclides. $^{55}$Co, $^{60}$Cu, $^{61}$Cu, $^{62}$Cu, $^{66}$Ga, $^{68}$Ga, $^{82}$Rb, and $^{86}$Y are examples of positron-emitting radionuclides. $^{64}$Cu is a beta- and positron-emitting radionuclide.

Nanoparticles useful in the present invention include particles having a size ranging from 1 to 1000 nm. Nanoparticles include, but are not limited to, beads, metallic particles or can in some cases be micelles, liposomes or other vesicles, or dendrimers. Other nanoparticles include carbon nanotubes and quantum dots. Nanoparticles can be packed with diagnostic and/or therapeutic agents.

In some embodiments, radical $X_2$ of formula I can be Gly, Ala, Sar or β-alanine, and stereoisomers thereof. Similarly, radical $X_6$ can be Val, Leu, Ile, Met, Phe, Asn, Glu, Gln, His, Lys, Arg, Asp, Gly, Ala, Ser, Thr, Tyr, Trp, Pro, Aad, Bec, Bmc, Bmp, Phe(4COOH), Hyp, HoSer, Tha, Ahch, Actp, Akch, Tyr(diI), Trp, Thz, 2Thi, 3Thi, Cit, HoCit, Aib, Nglu, or Fua, and stereoisomers thereof. In addition, radical $X_7$ can be Val, Leu, Ile, Met, Phe, Asn, Glu, Gln, His, Lys, Arg, Asp, Gly, Ala, Ser, Thr, Tyr, Trp, Pro, Bmp, HoSer, Nglu, HoCit, Bec, Aad, Hyp, Ahch, Phe(4COOH), Akch, Aecc, Abu, Phe(3,4-diOMe), Cpa, 2Thi, 3Thi, Thz, Phg, Phe(4-NO$_2$), Nle, (NMe)Phe, Aic, Chg, Bta, Bpa, Nal2, Nal1, Tic, Ppca, Cha, Bipa, Deg, Dpg, Acpc, Bmc, Cit, Sar, Tha, Pra, Actp, Aib, Agl, Acbc, Fua, Nva, Trp, Bug, Ach, (NMe)Val, Cpeg, (CαMe)Phe, Tyr(diI), Phe(2-Cl), Bua, HoPhe, HoLeu, Sta, Ing, Phe(4-CF$_3$), Oic, Dpa, Phe(4-t-Bu), HoCha or Phe(3, 4-diCl), and stereoisomers thereof. In other embodiments, each of radicals X₂, X₆ and X₇ can be a D-amino acid.

In other embodiments, the peptide ligand of the scaffold of the present invention can have formula Ia:

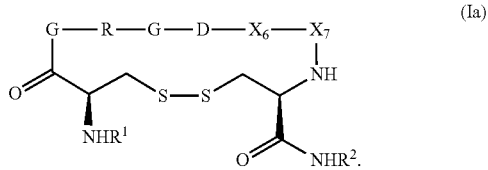
(Ia)

Radicals R¹ and R² of formula Ia are as described above. In some embodiments, radical X₆ can be DSer, DAsp, Ahch, Bmp, DGlu, Nglu or DCit, and radical X₇ can be DPhe, DGlu, DSer, DBug, DBta, DVal, DAglDPra, D(NMe)Val, D(CαMe)Val, DAbu, DIng, DIle, Actp, DTha, DAsp, DNal1 or Ppca. In some other embodiments, radical X₆ can be DAsp or DSer, and radical X₇ can be DGlu, DPhe, DSer, DVal, DBug or DBta.

R¹ and R² of formula Ia can each independently be H or C₁₋₆ alkyl. In some embodiments, Ie is H. In some embodiments, R² is H. In some embodiments, Ie and R² are both H.

X⁶ of formula Ia can be DSer, DAsp, DGlu, or DCit. X⁷ of formula Ia can be DPhe, DGlu, DSer, DBug, DBta, DVal, DAgl, DPra, D(NMe)Val, D(CαMe)Val, DAbu, DIng, DIle, DTha, DAsp, or DNal1. In some embodiments, X⁶ is DAsp and DSer. In some embodiments, X⁷ is DGlu, DPhe, DSer, DVal, DBug, or DBta.

In another embodiment, the peptide ligand of the present invention can be cGRGDsfc, cGRGDdfc, cGRGDsec, cGRGDdsc, cGRGDd-DBug-c, cGRGDd-DBta-c, cGRGDd-DBta-c, cGRGDdvc, CGRGDdvc, cGRGDdvC, CGRGDdvC, DPen-GRGDdv-DPen, DPen-GRGDdvc, cGRGDdv-DPen, Ac-cGRGDdvc, (β-alanine)-cGRGDdvc, (Ebes)-cGRGDdvc, caRGDdvc, c-Sar-RGDdvc, c-f3-alanine-RGDdvc, cG-HoArg-GDdvc, cG-Agp-GDdvc, cG-Agp-GEdvc, cGRGDd-DAgl-c, cGRGDd-DPra-c, cGRGDd-DBug-c, cGRGDd-D(NMe)Val-c, cGRGDd-D(CαMe)Val-c, cGRGDd-DAbu-c, cGRGDd-DIng-c, c-Sar-RGD-Ahch-ic, c-Sar-RGD-Ahch-DBug-c, cGRGDd-DAgl-C, C-Sar-RGDd-DPra-C, C-Sar-RGDd-Actp-C, c-Sar-RGDd-DPra-C, c-Sar-RGDd-Actp-C, CGRGDd-DTha-C, cGRGDd-DPra-C, cGRGDd-Actp-C, c-Sar-RGD-Ahch-iC, c-Sar-RGD-Ahch-DBug-C, C-Sar-RGD-Bmp-dC, CGRGDe-Ppca-c, cGRGD-Nglu-Ppca-c, cGRGDd-DNal1-c orcGRGDd-DBta-c. In other embodiments, the compound of the present invention can be cGRGDsfc, cGRGDdfc, cGRGDsec, cGRGDdsc, cGRGDdvc, cGRGDd-DBug-c or cGRGDd-DBta-c.

In another embodiment, the peptide ligand of the present invention can be cGRGDsfc, cGRGDdfc, cGRGDsec, cGRGDdsc, cGRGDdvc, CGRGDdvc, cGRGDdvC, CGRGDdvC, caRGDdvc, c-Sar-RGDdvc, c-f3-alanine-RGDdvc, cGRGDd-DAgl-c, cGRGDd-DPra-c, cGRGDd-DBug-c, DPen-GRGDdv-DPen, DPen-GRGDdvc, cGRGDdv-DPen, cGRGDd-D(NMe)Val-c, cGRGDd-D(CαMe)Val-c, cGRGDd-DAbu-C, cGRGDdic, cGRGDd-DIng-c, c-Sar-RGD-Ahch-ic, c-Sar-RGD-Ahch-DBug-c, cGRGDd-DAgl-C, C-Sar-RGDd-DPra-C, C-Sar-RGDd-Actp-C, c-Sar-RGDd-DPra-C, c-Sar-RGDd-Actp-C, CGRGDd-DTha-C, cGRGDd-DPra-C, cGRGDd-Actp-C, c-Sar-RGD-Ahch-iC, c-Sar-RGD-Ahch-DBug-C, C-Sar-RGD-Bmp-dC, CGRGDe-Ppca-c, CGRGD-Nglu-Ppca-c, CGRGDd-DNal1-C, CGRGDd-D3Thi-Ppca-c, cGRGDd-DBta-c, cG-HoArg-GDdvc, cG-(NMe)Arg-GDdvc, cGR-Sar-Ddvc, cGRG-(NMe)Asp-dvc, cG-Agp-GDdvc, cG-Agp-GEdvc, cGRGDsdC, cGRGDd-DIng-c, cGRGDd-DNal1-c, cGRGDd-DNal2-c, cGRGDd-D3Thi-c, cGRGDd-D2Thi-c, cGRGDdwc, cGRGDd-DTha-c, cGRGD-DCit-Ppca-c, cGRGDe-Ppca-c, cGRGD-NGlu-Ppca-c, cGRGD-DCit-DBta-c, cGRGD-DBec-Ahch-c, or cGRGD-DBec-DPra-c. In some embodiments, the peptide ligand is cGRGDdvc (LXW7).

The peptide ligand of the scaffold functions to increases the attachment of endothelial cells and/or endothelial progenitor cells. The peptide ligand can have an affinity for a cell surface integrin. The integrin can regulate retention, mobilization, vascularization, or enothelialization of cells. In some embodiments, the peptide ligand binds to one or more of integrins α4β1, α5β1, α6β1, αvβ3 and αvβ5. In some embodiments, the peptide ligand binds to integrin αvβ3 on the cells.

The provided scaffold preferably has the desirable characteristics of good biocompatibility, easy molding, good degradation, osteoconductivity, an adequate pore size and porosity, and suitable mechanical strength. It is beneficial that the scaffold material be easily sculpted or molded to be processed into a variety of sizes and shapes. It is also advantageous if the degradation products of the scaffold pose as little negative side effects as possible for an implantation subject. Having an appropriate pore size and porosity can allow good mass transport of nutrients and other factors required by the implanted cells. A suitable mechanical strength can prevent damage to the scaffold by surrounding tissue or fibrous tissue ingrowth. The scaffold can be, for example, a calcium phosphate ceramic or a polymer. The scaffold can include multiple layers, each with a different compositions and function.

The scaffold can include a biocompatible polymer or biopolymer. The scaffold can be a medical device, and the polymer of a scaffold can be a component of the medical device or the device itself. The scaffold or device can be suitable for intraluminal or extraluminal positioning or operation. In some embodiments, the polymer is hydroxyapatite. In some embodiments the polymer of the scaffold is poly (L-lactic acid) (PLLA), polycaprolactone (PCL), poly (lactic-co-glycolic acid) (PLGA), hydroxyapatite (HA), poly (lactide-co-ε-caprolactone) (PLCL), polytetrafluoroethylene (PTFE), expanded polytetrafluoroethylene (ePTFE), or combinations thereof. In some embodiments, the polymer is ePTFE. In some embodiments, the polymer is a hybrid polymer or copolymer.

Biopolymers useful in the present invention can have a functional group that can undergo chemoselective ligation with a complementary functional group in the presence of a plurality of similar functional groups. For example, and not by way of limitation, a primary alcohol can be selectively reacted in the presence of secondary alcohols. In a similar manner, a polyamine biopolymer could have both primary and secondary amines, wherein only the primary amines undergo chemoselective ligation with an appropriate complementary functional group. Other similar functional groups with a preference in reactivity for one over the other could be aldehydes and ketones. In some cases, the biopolymer does not itself comprise a functional group for chemoselective ligation, but can be subsequently derivatized with a functional group for chemoselective ligation.

The polymer of the scaffold can further include a coating. The peptide ligand can be covalently attached to the coating. In some embodiments, the coating is a parylene polymer. The parylene polymer can be conformally coated onto the polymer by a vapor deposition process. In some embodiments, the polymer is activated using microwave plasma or ultraviolet radiation prior to coating with parylenes. In some embodiments, the parylene polymer is Parylene A, Parylene C, Parylene D, Parylene HT, or Parylene N. The parylene polymer can also be a functionalized parylene, such as tricyclo[8.2.2.24,7]hexadeca-4,6,10,12,13,15-hexaene-5-carboxaldehyde (CAS: 729-30-6), tricyclo[8.2.2.24,7]hexadeca-4,6,10,12,13,15-hexaene-5-amine (CAS: 10122-95-9), tricyclo[8.2.2.24,7]hexadeca-4,6,10,12,13,15-hexaene-5-carboxylic acid (CAS: 18931-39-0), or other parylenes functionalized with one or more of aldehyde groups, ester groups, alcohol groups, anhydride groups, alkyne groups, phenylacetyl groups, or other functional groups. Further descriptions of parylene coatings in medical devices and implants can be found in, for example, Kuppusami and Oskouei (2015) *Universal J. Biomed. Eng.* 2015:9, and Tan and Craighead (2010) *Materials* 3:1803, both of which are incorporated in their entirety for all purposes.

Cells can be seeded onto the scaffold prior to or subsequent to implantation in a subject. In some embodiments, endothelial cells, endothelial progenitor cells, and/or osteogenic cells are seeded on the scaffold. In some embodiments, the scaffold is seeded with cells that are derived from adipose stem cells (ASCs). In some embodiments, ASC-derived endothelial cells and osteoblasts are used to sequentially seed the scaffold. The ASC-derived endothelial cells can form a vascular network within a bony construct of the scaffold, while the ASC-derived osteoblasts can increase bone regeneration.

IV. Engineered Tissues

Tissue engineering methods can include adsorbing onto normal tissue cells a scaffold with in vitro biocompatibility that has been seeded with desired cell types. Such a porous scaffold can then degrade and be absorbed by the body. The results of this process can include the implantation of cells that were delivered into an injury site of the body along with a composite biodegradable material. It is preferable that the material, such as a scaffold, also promote the growth, reproduction, and/or differentiation of implanted cells. This can enable the gradual formation of the morphology and function necessary for engineered tissues to act as alternatives for damaged tissues and organs, achieving the purpose of rehabilitation and reconstruction. In some embodiments, the present invention provides engineered tissues comprising a scaffold of the present invention.

V. Methods of Improving Endothelialization and Vascularization

The present invention provides several methods of improving endothelialization and vascularization for engineered tissues. The methods include implanting a scaffold of the present invention into a subject. The cells can include endothelial cells and/or endothelial progenitor cells. In some embodiments, the method includes implanting a scaffold having a peptide ligand that increases the recruitment of endothelial cells and/or endothelial progenitor cells to the scaffold. In some embodiments, the method includes implanting a scaffold having a peptide ligand that increases the proliferation and integration of transplanted endothelial cells and/or endothelial progenitor cells on the scaffold.

VI. Methods of Repairing a Bone Defect

Treatment of bone defects is a very common clinical problem, as bone defects can present a great inconvenience for a patient, seriously affecting his or her daily life. Clinical treatment methods typically include autogenous bone graft or allografts, although with the latter there is a limited risk of disease transmission and immune rejection by donor. The use of tissue engineering methods for preparing a bone substitute can avoid some of these problems and promote bone regeneration for the treatment of bone defects.

Large and complex bone defects may exceed the body's ability to regenerate and surgical repair of such defects remains a particular challenge. Current surgical treatment of large bone defects involves the use of either autologous bone grafts or alloplastic materials. Although these approaches are in large part successful, they come with inherent disadvantages. For example, alloplastic materials have problems with rejection, infection, and autologous bone grafts are often limited in availability and donor site morbidity. Thus, there remains a pressing need for a suitable alternative to currently available techniques for bone repair. Tissue engineered bony constructs have the potential to overcome the shortcomings of current methods. However, the survival of large and complex constructs relies on a sophisticated vascular network for efficient and immediate nutrient delivery. In the absence of a vascular network, the seeded cells far from the blood supply die, ultimately jeopardizing the survival of the whole construct.

The present invention provides several methods of repairing a bone defect in a subject. The methods include implanting a scaffold of the present invention into a subject. In some embodiments, the bone defect is a calvarial bone defect. In some embodiments, endothelial cells and/or osteogenic cells are seeded on the scaffold prior to the implantation of the scaffold into the subject. In some embodiments, endothelial cells and/or osteogenic cells are seeded on the scaffold subsequent to the implantation of the scaffold into the subject.

VII. Coatings

The present invention also provides several coatings for the modification of scaffolds and medical devices. The coating can promote the endothelialization of the surface to which it is applied, thereby increasing the regenerative or growth potential of cells on the scaffold. The coated surface can be any material, including a polymer, a plastic, a metal, or glass. As an example, the scaffold can be in the form of a vascular graft, and the coating of the vascular graft can enable the generation of a self-renewable endothelium on the graft luminal surface. The coating can also be applied to a wide range of intravascular devices, including cardiac valves and catheters.

The coated products can be used for hemodialysis, a procedure for which a functioning vascular access is a necessity. The most common current form of hemodialysis vascular access involves the use of arteriovenous PTFE dialysis grafts. These grafts can have high failure rates, however, due to complications such as thrombosis, stenosis, and infection. By promoting the formation of a functional endothelium to the graft scaffolds, the provided coating can add or improve several beneficial properties of the grafts. These include anti-adhesion properties, anti-inflammatory and immune responses, cellular proliferation promotion, smooth muscle tone mediation, and hemostatic regulatory molecule production.

The provided coating includes any of the peptide ligands described above. In some embodiments, the coating includes the ligand LXW7. The coating further includes a polymer such as a parylene polymer. Parylene is most current coating polymer associated with implantable medical devices and grafts because it possesses excellent mechanical properties in terms of flexibility and long-lasting in vivo adherence to the implant surface. Parylenes can be conformally coated onto irregular substrates by a chemical vapor deposition (CVD) process, and are chemically inert, nonbiodegradable, and essentially substrate-independent. The FDA has approved parylenes as Class VI polymers for coating medical devices due to their biocompatibility. In some embodiments, the parylene polymer is Parylene C, Parylene D, Parylene HT, or Parylene N. In some embodiments, the device or scaffold is first coated with a parylene polymer. The parylene can be functionalized either before or after the coating is applied. Subsequent to the functionalization of the parylene, it can be conjugated with a ligand such as LXW7. In some embodiments, the ligand is conjugated to the coating polymer before the this polymer is used to coat the scaffold or device. In some embodiments, the scaffold or device surface is activated using microwave plasma prior to coating. In some embodiments, the scaffold or device surface is exposed to ultraviolet radiation, inducing photochemical covalent coupling of the surface and the coating. In some embodiments, the coated surface is cured by exposure to, for example, an elevated temperature or ultraviolet radiation subsequent to the application of the coating. In some embodiments, functionality is added to the scaffold or device surface in an activation process performed prior to the coating. A graft polymer is then added to the functionalized surface and used to support further polymer growth, thereby generating the coating polymer.

The coating or scaffold polymer can be functionalized using any suitable chemistry to facilitate covalent attachment of the polymers to one another, or of the ligand or an attached linker to either of the polymers. For example, the polymer can be functionalized with aldehyde groups that can react with primary amines on the ligand or linker. The polymer can be functionalized with glycidoxy groups that can react with amines on the ligand or linker. The polymer can be functionalized with succinimidyl groups that can crosslink with amines on the ligand or linker. The polymer can be functionalized with isocyanate groups that can be covalently ligated to amines on the ligand or linker. The polymer can be functionalized with maleimide groups that can react with thiols on the ligand or linker. The polymer can be functionalized with chlorine groups that can covalently attach to alcohol groups on the ligand or linker. The polymer can be functionalized with glyoxylyl groups that can covalently attach to the ligand or linker via oxime bonds or thiazolidine ring formation. The polymer can be functionalized with thioester groups that can form amide bonds with N-terminal cysteines of the ligand or linker. The polymer can be functionalized with quinone groups that can react with cyclodienes introduced into the ligand or linker. Other suitable chemistries can be similarly applied to covalently conjugate the ligand or linker to the polymer.

The functionalization of the coating polymer can include the introduction of alkyne functional groups. In some embodiments, a parylene polymer of the coating is modified to produce alkyne-functionalized parylene, which is then covalently ligated to an LXW7-linker-azide via Click chemistry. In some embodiments, the polymer base (e.g., ePTFE) of a scaffold or device is activated (e.g., by microwave plasma) prior to being coated with an alkyne-functionalized coating polymer (e.g., parylene). This coating can be through, for example, a CVD process. The ligand-linker-azide (e.g., LXW7-linker-$N_3$) can then be immobilized onto the surface to complete the coating. In alternative embodiments, the ligand-linker-azide and functionalized coating polymer are conjugated prior to the application of the coating to the scaffold or device.

VIII. Examples

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1. Cell Culture and Platelet Isolation

Endothelial colony forming cells (ECFCs), a subtype of EPCs also often referred to as outgrowth endothelial cells (OECs), were isolated from human umbilical cord blood as previously described (Williams et al. (2015) *PloS One* 10:e0123437; Ingram et al. (2004) *Blood* 104:2752). Human umbilical cord blood (10 U heparin/mL blood) was obtained from the UC Davis Umbilical Cord *Blood* Collection Program (UCBCP) and diluted 1:1 with Phosphate-buffered saline (PBS), without calcium and magnesium, pH 7.2 (Hyclone). Fifteen mL Ficoll-Paque PLUS (Amersham Biosciences) was laid at the bottom of 20 mL diluted blood and centrifuged at 2000 rpm for 30 minutes at room temperature. The hazy layer of mononuclear cells (MNCs) that seat at the interface between the Ficoll and serum was collected and dispensed into 50-mL conical tube containing 10 mL EBM-2 (Lonza) and centrifuged at 1500 rpm for 10 minutes at room temperature. The supernatant was carefully aspirated and the pellets were treated with red blood cell lysis buffer (eBioscience, Inc.) and then sorted by CD34 microbead magnetic sorting (Miltenyi Biotec GmbH) as per manufacturer's instructions. The $CD34^+$ cells were seeded on rat-tail collagen I (BD Biosciences Discovery) coated tissue culture plates and cultured in EGM-2 media (Lonza). After 24 h, non-adherent cells were removed and the media was changed daily to day 7 and every other day thereafter. ECFC-derived colonies appeared between day 4 and day 7 of culture with s typical endothelial cobblestone pattern. Individual colonies were isolated and expanded and allowed to grow to 80% to 90% confluency before first passage. ECFCs were used between P3 and P5 for all experiments.

Human coronary artery endothelial cells (HCAECs) were purchased from ATCC. Human cardiac microvascular endothelial cells (HMVECs) were purchased from Lonza. THP-1 monocytes were obtained from Dr. Pamela Lein (University of California, Davis). The myeloid leukemia K562 cells that have been transfected with human integrin $\alpha v \beta 3$ gene ($\alpha v \beta 3$-K562 cells) were provided by Dr. Yoshikazu Takada and the K562 cells transfected with human integrin $\alpha IIb\beta 3$ gene ($\alpha IIb\beta 3$-K562 cells) were provided Dr. Jennifer Cochran (Stanford University)

HECFCs, HCAECs and HMVECs were cultured in EC expansion medium EGM-2 and THP-1 monocytes were cultured in RPMI Medium 1640 (Gibco) supplemented with 10% fetal bovine serum (FBS, Hyclone) and 0.05 mM 2-mercaptoethanol (Sigma). $\alpha v \beta 3$-K562 cells and $\alpha IIb\beta 3$-K562 cells were cultured in RPMI Medium 1640 plus 10% FBS. Platelet-rich plasma (PRP) was obtained from UC Davis Medical Center (Sacramento, Calif.). Fresh PRP ($260 \times 10^3$ platelets/$\mu L$) was centrifuged, and the pellets were resuspended in Dulbecco's Phosphate Buffer Saline (DPBS;

Hyclone) containing 2 mM $CaCl_2$) and $MgCl_2$ to a final concentration of $1\times10^8$ platelets/mL.

Example 2. EPC/EC-Bead and Platelet-Bead Binding Assay

HECFCs, HCAECs, HMVECs and THP-1 monocytes were cultured in their respective growth medium as described in Example 1. For cell bead-binding assay, $6\times10^5$ HECFCs, HCAECs, HMVECs or THP-1 monocytes in 2 mL of their respective culture medium were added to an ultra-low attachment 35-mm petri dish (Corning Incorporated) followed by resin beads (Lam et al. (1991) *Nature* 354:82). The dishes were incubated in a shaking incubator at 37° C., 5% $CO_2$ for various time points at 40 rpm. For platelet bead-binding assay, the platelets isolated as described in Example 1 were added to an ultra-low attachment 35-mm petri dish and incubated with the resin beads in the shaking incubator as described for the cell-bead binding assy. Phase contrast images were taken at different time points using an Olympus IX81 microscope.

Example 3. ECs and Platelets Attachment Assay

Ligands LXW7, LXY30, and LLP2A were synthesized as in U.S. Pat. No. 9,073,974. Biotinylated LXW7 (LXW7-bio) and biotinylated GRGD (GRGD-bio) (SEQ ID NO: 1) were synthesized using established solid phase peptide synthesis protocols (Xiao et al. (2010) *Mol Cancer Therapeutics* 9:2714). Peptide-bio was designed to have biotin attached to the side chain of Lys, with two hydrophilic linkers between peptide and Lys (biotin). To modify culture surface with ligands, target culture wells in a 24-well plate were coated with 500 µL of 20 µg/mL Avidin (Thermo Fisher Scientific), and incubated for 1 hour at 37° C. Avidin coated wells were rinsed three times with DPBS and were treated with 500 µL molar equivalents (2 µM) of D-biotin (Thermo Fisher Scientific), LXW7-bio, or GRGD-bio (SEQ ID NO: 1). After 1 hour, the wells were washed three times with DPBS and blocked with 1% bovine serum albumin (BSA; Thermo Fisher Scientific) for 1 hour. After the wells were rinsed three times with DPBS, for cell attachment assay, $5\times10^4$ HCAECs and THP-1 monocytes suspended in the respective maintenance medium were added to the wells and incubated for 10 minutes or 16 hours at 37° C., 5% $CO_2$, respectively. After each time point the wells were washed three times with DPBS, and the adhered cells were fixed in 10% formalin (Azer Scientific) for 20 minutes. For platelets attachment assay, the PRP was centrifuged, and the platelet pellet was resuspended in 1% BSA with 2 mM $CaCl_2$ and 1 mM $MgCl_2$ to achieve a final concentration of $1\times10^8$ platelets/mL, added to the wells at a density of $5\times10^7$ platelets/cm$^2$, and incubated for 16 hours at 37° C., 5% $CO_2$. The wells were washed three times with DPBS, and the adhered cells were fixed in 10% formalin for 20 min. The HCAECs wells were washed with DPBS again and blocked for 1 hour with 1% BSA. An additional wash was performed, and the plate was incubated overnight with mouse anti-PECAM-1 antibody (1:100; Abcam) in 1% BSA at 4° C. The wells were washed and incubated with goat anti-mouse Alexa Fluor 594 conjugate (1:500; Life Technologies) in 1% BSA for 1 hour at room temperature and then nuclei were stained with 4',6-diamino-2-phenylindole (DAPI). After three times of washing with DPBS, the cells were imaged using an Olympus IX81 microscope. Five images were randomly taken from each sample and quantification of images was performed using the Image J software (NIH).

Example 4. Flow Cytometry Analysis of Ligand-Cell Binding Affinity

LXW7-bio (1 µM) was incubated with $3\times10^5$ HECFCs, HCAECs, HMVECs, αvβ3-K562 and αIIbβ3-K562 cells and THP-1 monocytes and $1\times10^8$ platelets in binding buffer (HEPES containing 10% FBS) on ice for 30 minutes. The samples were washed three times with DPBS containing 1% FBS and incubated with 2 µg/ml of streptavidin-phycoerythrin on ice for 30 minutes and then washed with DPBS. Samples were analyzed on a BD Fortessa LSR Cell Analyzer and further data analysis and gating were performed using FlowJo software (Treestar, Inc.).

Example 5. MTS Assay of EC Proliferation on LXW7

The 96-well plates from Example 3 were treated with 1 µM Avidin solution for 1 hour at room temperature. Avidin coated wells were rinsed three times with DPBS and treated with LXW7-bio (1 µM), with D-biotin (1 µM) serving as the control. After 1 hour, the wells were washed three times with DPBS and blocked with 1% BSA for 1 hour. $3\times10^3$ viable HCAECs were seeded per well and cultured in EGM-2 media for 5 days. MTS assay was performed at each day as per the manufacturer instructions (Interchim) and analyzed on SpectraMax-3 plate reader (Molecular Devices).

Example 6. Western-Blot Analysis

The 100-mm dishes from Example 2 were treated with Avidin followed by LXW7-bio or D-biotin as described in Example 5. $8\times10^5$ HCAECs were seeded per dish and cultured in EGM-2 media for 4 days. Cells were lysed using Extraction Kit (Thermo Fisher Scientific) and protein concentrations were determined using BCA Protein Assay (Thermo Fisher Scientific). Fifteen µg of each sample were loaded and separated using a 4-12% Bis-Tris NuPAGE gel (Thermo Fisher Scientific) and transferred to a nitrocellulose membrane. The membrane was blocked in 5% BSA in TBST (Tris-buffered saline with 0.5% Tween-20), and subsequently incubated with primary antibodies anti-VEGF Receptor 2, anti-Phospho-VEGF Receptor 2, anti-p44/42 MAPK (Erk1/2) and anti-Phospho-p44/42 MAPK (Erk1/2) (Thr202/Tyr204), all purchased from Cell Signaling Technologies, in 1% BSA overnight at 4° C. After washing three times with TBST, the membranes were incubated with respective horseradish peroxidase-conjugated secondary antibodies in 1% non-fat dry milk in TBST (BioRad) for 1 hour at room temperature. After washing, the protein bands were visualized using West Dura Substrate (Thermo Fisher Scientific) and quantified using Image J software.

Example 7. Preparation of LXW7 Modified Biomaterial Scaffolds

Poly (L-lactic acid) (PLLA) (MW 67,400, Sigma Aldrich) and polycaprolactone (PCL, MW 2,000, Polysciences) were used to fabricate electrospun microfibrous biomaterial scaffolds. Polymer blends (e.g., 19% PLLA and 5% PCL; w/v) were completely dissolved in 1,1,1,3,3,3-hexafluoro-2-propanol (HFIP, Aladdin). Microfibrous membranes with thickness of about 200 µm were prepared by electrospinning polymer fibers onto to the rotating drum collector. A negative voltage of 4.5 kV was applied to the mandrel, and a positive voltage of 4 kV was applied to the spinneret by using a high voltage generator (Gamma High Voltage).

Figure 2:
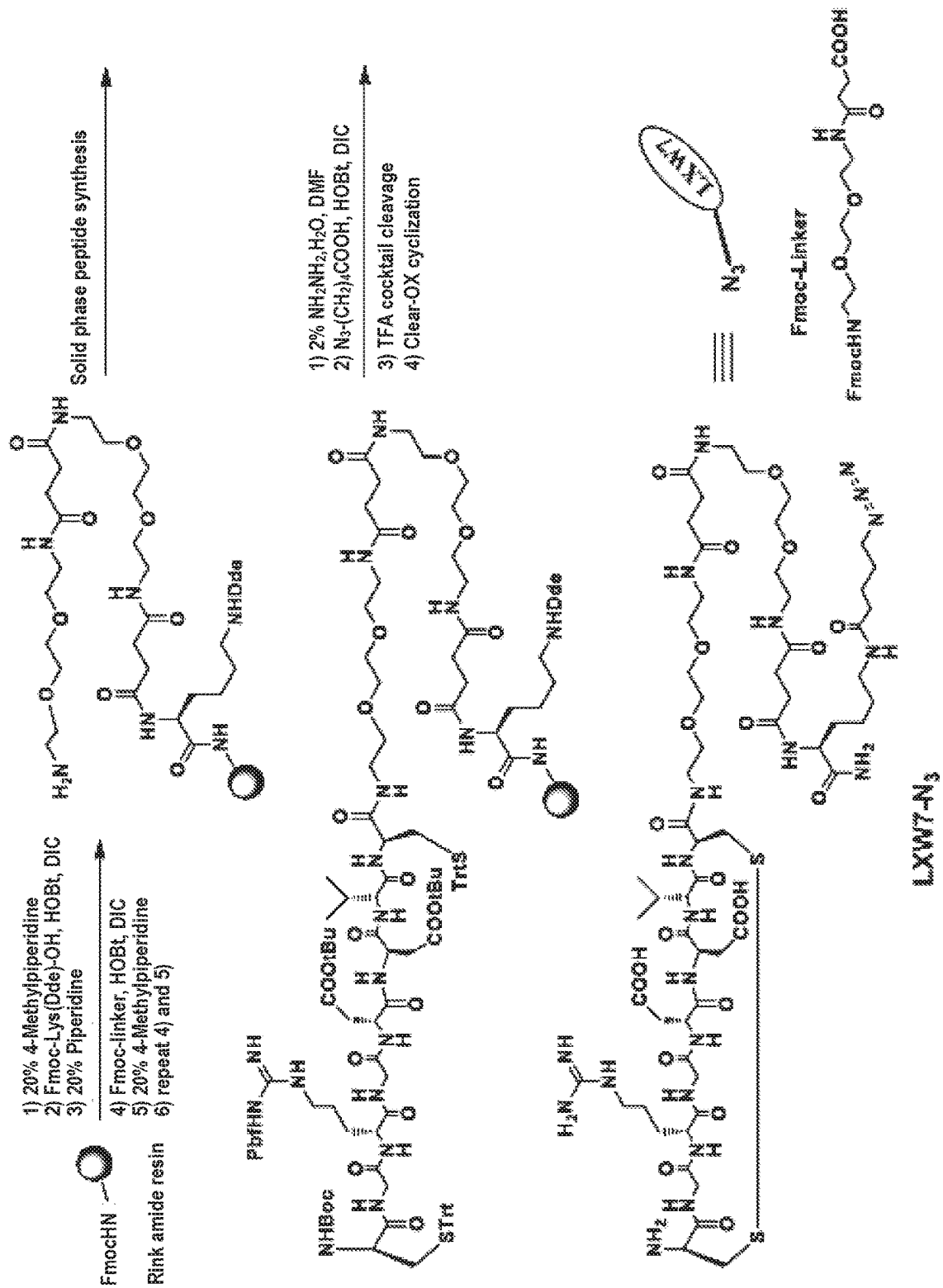
FIG. 2 presents a synthetic scheme for the ligand LXW7-N$_3$.

LXW7 was grafted onto the PLLA/PCL membrane surface through three steps. Membranes were incubated in 0.01N sodium hydroxide for 10 minutes to expose the carboxyl groups on the surface. The membranes were then further incubated in solution of 1-ethyl-3-(3-dimethylaminopropyl) carbodiimide hydrochloride (EDC) and N-hydroxysulfosuccinimide (sulfo-NHS) (Thermo Fisher Scientific) in 0.5 M morpholino ethane sulfonic acid (MES) buffer (pH 5.5, Thermo Fisher Scientific) for 30 minutes. After brief washing with DPBS, the membranes were incubated in a solution of $H_2N$-PEG-alkyne (MP 5000, Polysciences, Inc.) in DPBS for 2 hours on a shaker. Lastly, azido derivatized LXW7 (LXW7-$N_3$), synthesized via a similar approach as LXW7-bio but with a 5-azidopentanoic acid attached to the side chain of lysine (FIG. 2), was conjugated to alkyne-decorated membranes via Click chemistry in the presence of 5 µM $CuSO_4.5H_2O$, 50 µM sodium ascorbate, Cu powder, and N,N-Diisopropylethylamine (DIEA) (all from Sigma) in water system for 6 days (Nandivada et al. (2006) *Angewandte Chemie* 45:3360).

The structure of the membranes was characterized with a scanning electron microscope (SEM, Hitachi TM-1000). Attenuated total reflection spectra of the untreated, PEG only modified, and PEG-LXW7 modified membranes were obtained using an Attenuated Total Reflectance-Fourier transform infrared (ATR-FTIR) spectrometer (PerkinElmer).

Example 8. Biomaterial Scaffold Modified with LXW7-Supported EC Attachment and Spreading LXW7-modified electrospun microfibrous membranes and untreated control membranes were placed in 35-mm tissue culture dishes. The membranes were rinsed with DPBS and incubated with HCAECs in EGM-2 media at a density of $5 \times 10^4$ cells/cm$^2$. After 2 hours incubation, the media was aspirated, and unattached cells were washed off with DPBS three times. The adhered cells were fixed in 10% formalin and immunostained with anti-PECAM-1 antibody (1:100; Abcam) and imaged using an Olympus IX81 microscope. Some of the cell samples were further cultured in EGM-2 media for 2 days and cell morphology and spreading on the microfibrous scaffold surface was characterized with SEM. The cell-covered area was quantified using Image J software.

Example 9. Statistical Analysis

For two-sample comparison, Student's t-test was used. For multiple-sample comparison, analysis of variance (ANOVA) was performed to detect whether a significant difference existed between groups with different treatments, and Tukey's multiple comparisons test was used for post-analysis. A p-value of 0.05 or less will indicate significant difference between samples in comparison.

Figure 3:
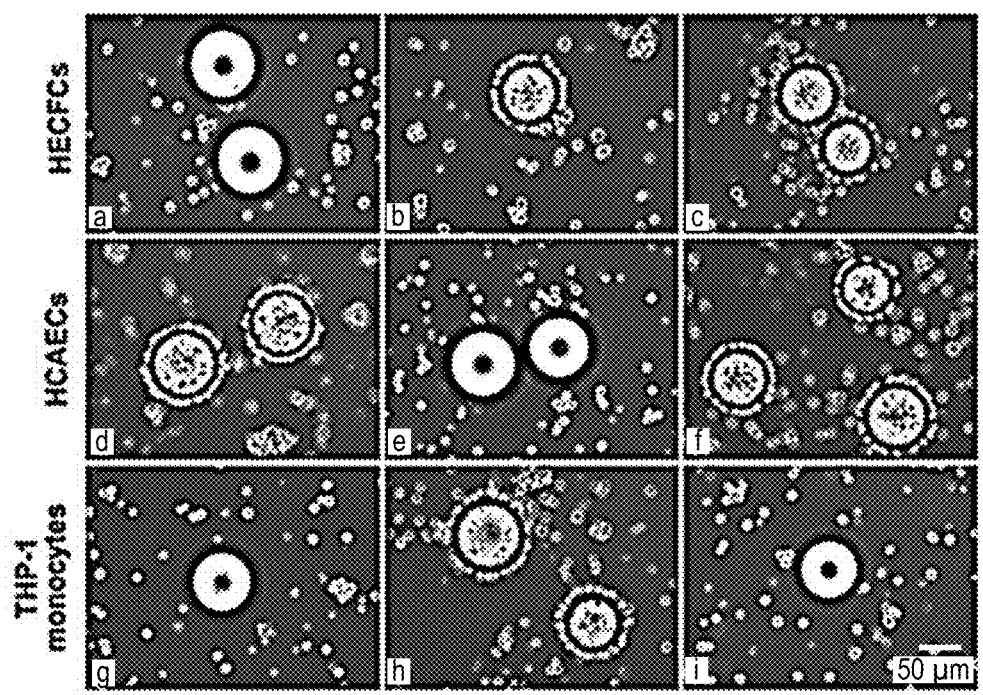
FIG. 3 presents images from an on-bead cell binding assay for testing EPC/EC binding affinity of ligands. HECFCs (a-c), HCAECs (d-f) and THP-1 monocytes (g-i) were incubated with resin beads displaying LXY30 (left panels), LLP2A (middle panels) and LXW7 (right panels). Scale bar=50 µm.
Figure 4:
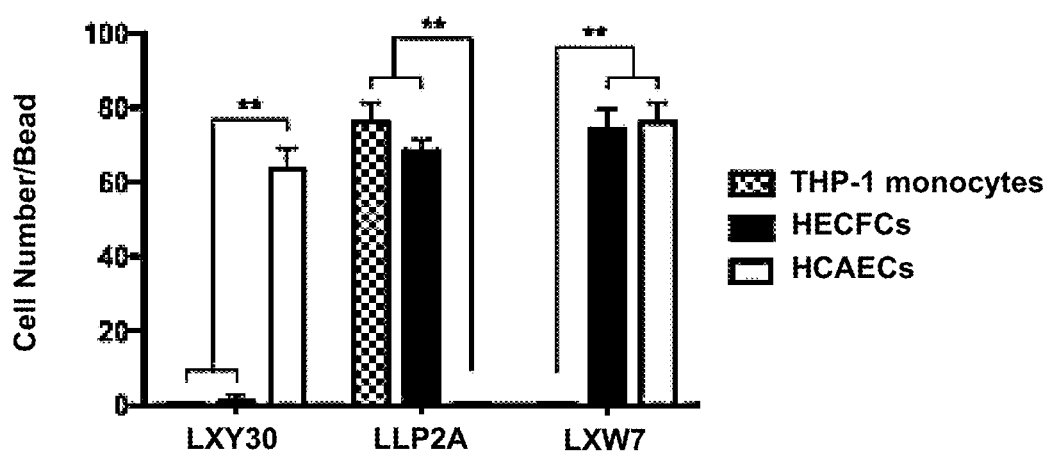
FIG. 4 is a graph of results from the on-bead cell binding assay of FIG. 3. The numbers of cells bound on beads displaying different types of ligands were quantified and statistical analyses were performed. Data were expressed as mean±standard deviation: **p<0.01 (n=3).

Example 10. Determination of Binding Affinity of Integrin-Targeting Peptide Ligands with EPCs/ECs Using On-Bead Whole Cell Binding Assay Three integrin-targeting ligands—LXY30 (α3β1), LLP2A (α4β1) and LXW7 (αvβ3)—were tested for their binding activities to EPCs and ECs. After 2 hours incubation, the results showed that LXY30 bound only to HCAECs (FIG. 3, d), but not to HECFCs or to THP-1 monocytes (FIG. 3, a and g). LLP2A bound to both HECFCs and THP-1 monocytes (FIG. 3, b and h), but not to HCAECs (FIG. 3, e). LXW7 bound both HECFCs and HCAECs (FIG. 3, c and f), but not to THP-1 monocytes (FIG. 3, i). Quantification of the number of cells bound on each bead showed that there were significant differences between different types of cells bound on each bead modified with different types of ligands (FIG. 4). LXY30 only bound to ECs, not to EPCs. LLP2A only bound to EPCs, not to ECs. LXW7 bound well to both EPCs and ECs. Based on these results, we selected LXW7 as the optimal candidate ligand and LXW7 was further characterized in the following experiments.

Example 11. Effects of LXW7 Concentration on Cell Adhesion

Figure 5:
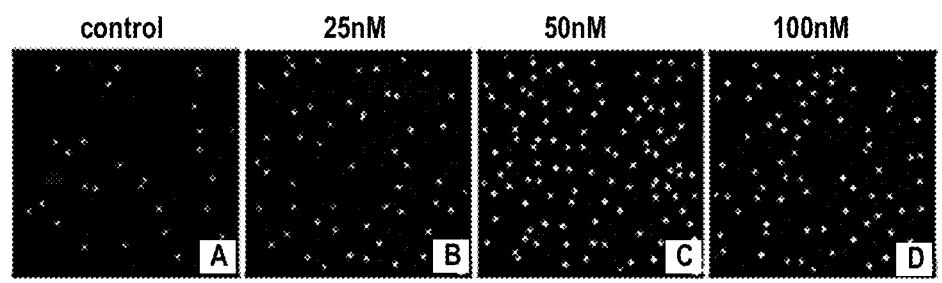
FIG. 5 presents nucleus images of adherent EPCs after seeding on PLCL membrane modified with LXW7 at different concentrations (0 nM, 25 nM, 50 nM, 100 nM) for 30 min.
Figure 6:
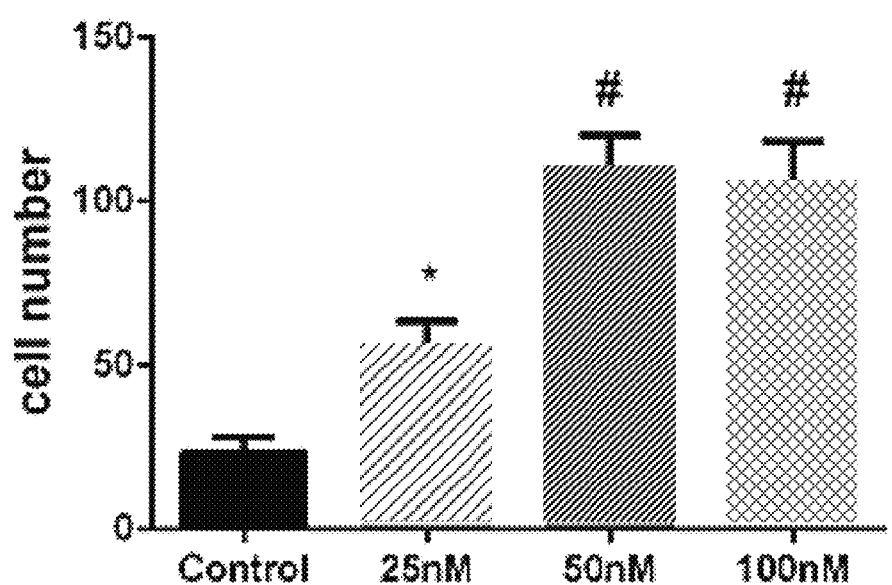
FIG. 6 is a graph of the number of EPCs attached on membranes of FIG. 5.
Figure 7:
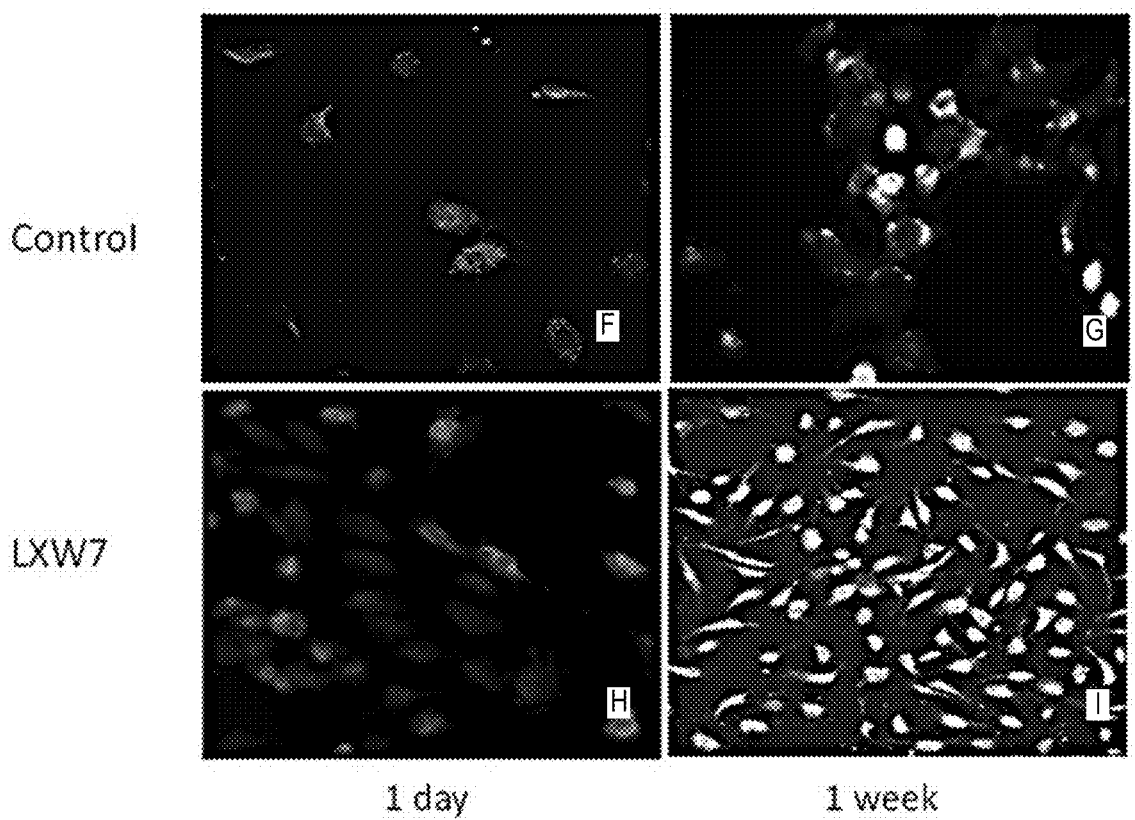
FIG. 7 presents adherent cell images on PLCL membranes (control and LXW7 50 nM) at 1 day and 1 week, magnifications 20×.

To optimize the effect of different LXW7 concentration modification on EPC adhesion, 1×105 cells were seeded on PLCL and surfaces modified by different concentration LXW7. Fluorescence images showed that the PLCL surface was almost no cells attachment (FIG. 5, A), whereas cells adhered on the LXW7-PLCL surfaces, and the 50 nM was the best attached surface (FIG. 5, B-D; FIG. 6, FIG. 7).

Example 12. Test of Binding Specificity of LXW7 to EPCs/ECs

Figure 8:
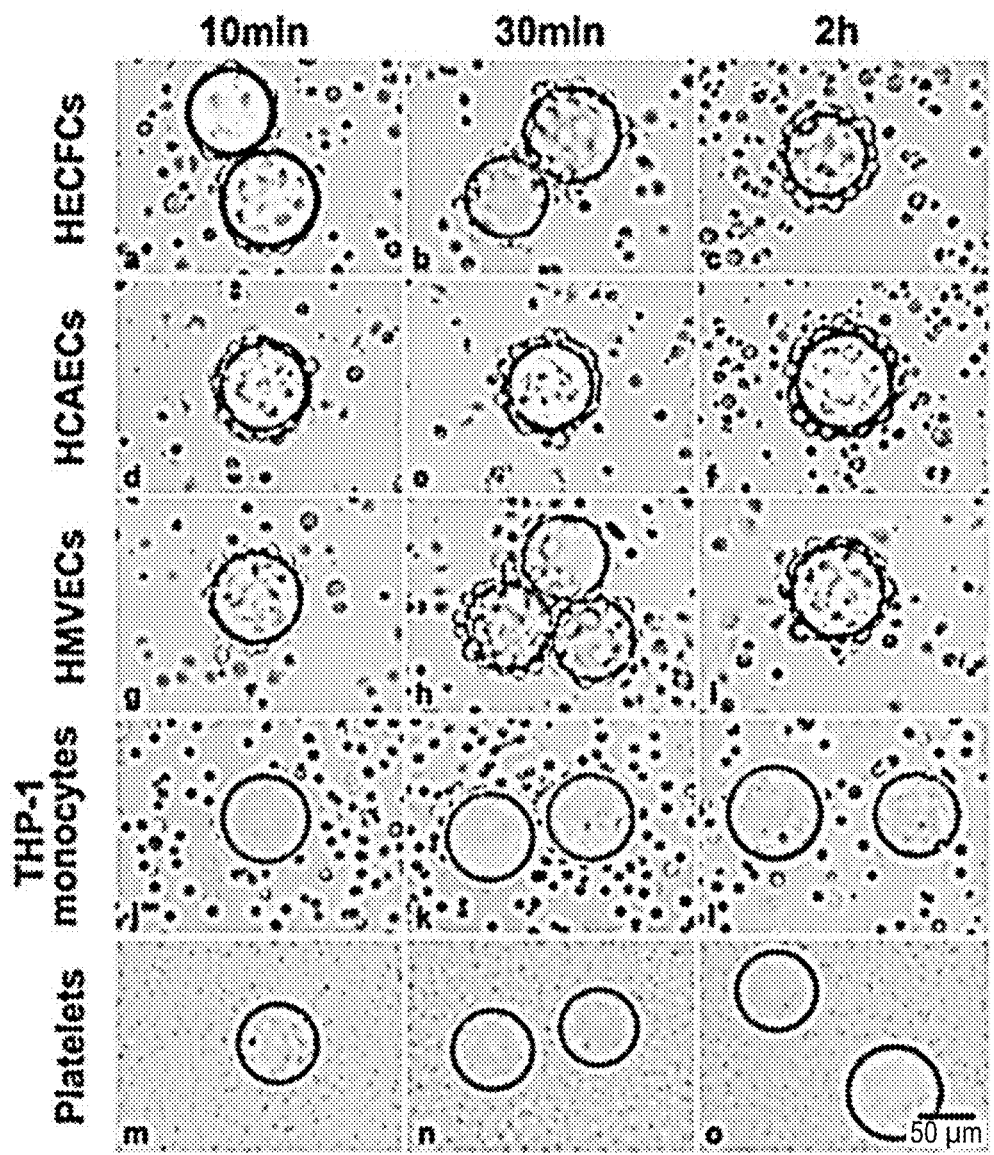
FIG. 8 presents images from an assay of binding specificity of LXW7 to EPCs/ECs. Beads displaying LXW7 were incubated with HECFCs (a-c), HCAECs (d-f), HMVECs (g-i), THP-1 monocytes (j-l), or platelets (m-o) for 10 minutes (left panels), 30 minutes (middle panels) or 2 hours (right panels). LXW7 efficiently supported EPC/EC attachment (a-i) but did not support effective attachment of THP-1 monocytes (j-l) or platelets (m-o). Scale bar=50 µm.
Figure 9:
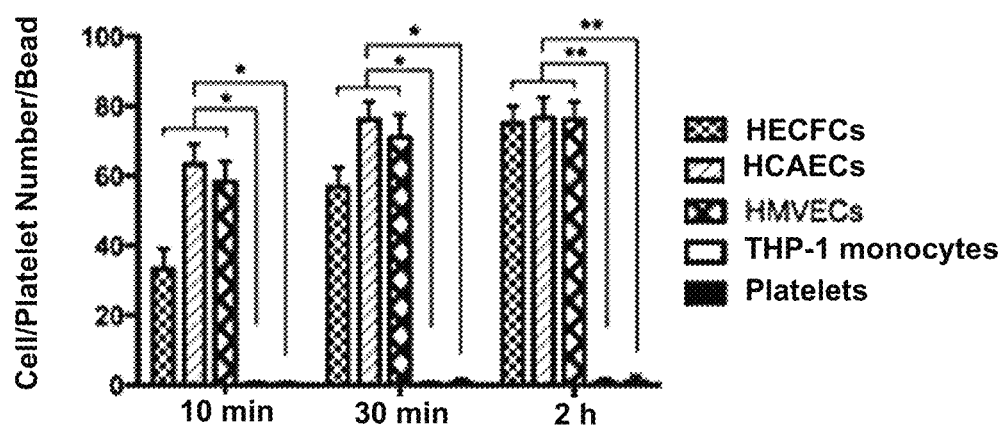
FIG. 9 is a graph of results from the binding specificity assay of FIG. 8. The number of different types of cells bound on each bead displaying LXW7 were quantified and statistical analyses were performed. Data were expressed as mean±standard deviation: *p<0.05, **p<0.01 (n=3).

Ligands with high binding specificity to EPCs/ECs not only support rapid cell attachment, but also potentially resist the attachment of other "off-target" cells, platelets and proteins. To confirm binding specificity of LXW7 to EPCs/ECs, resin beads displaying LXW7 were incubated with EPCs/ECs from different sources (HECFCs, HCAECs and HMVECs), THP-1 monocytes, and platelets. At different time points after incubation (10 minutes, 30 minutes or 2 hours), phase contrast images were taken to determine cell-bead binding affinity. We found that LXW7 efficiently supported attachment of EPCs/ECs from different sources, and that the number of cells attached to LXW7 beads increased over time (FIG. 8, a-i). Remarkably, LXW7 did not support effective attachment of THP-1 monocytes (FIG. 8, j-l) or platelets (FIG. 8, m-o). Quantification of the number of cells and platelets bound on each bead showed that there were significantly more EPCs/ECs from different sources (HECFCs, HCAECs and HMVECs), as compared to THP-1 monocytes and platelets, on beads displaying LXW7 (FIG. 9). These results demonstrate that LXW7 possesses strong binding specificity to EPCs/ECs.

Example 13. Comparison of LXW7 and RGD Binding Specificities and Affinities

Figure 10:
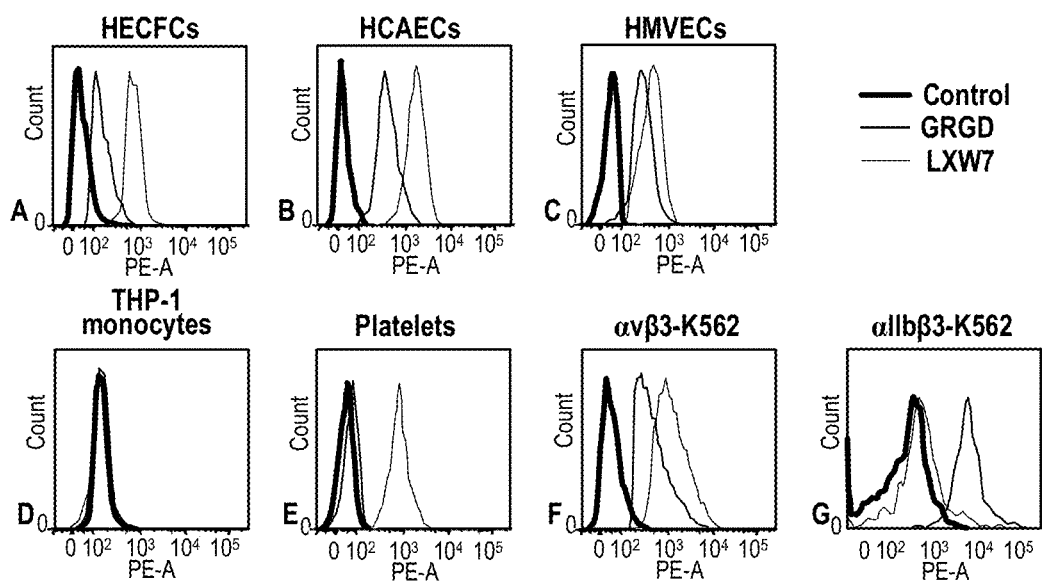
FIG. 10 presents flow cytometry data from an assay of binding affinity of LXW7 and GRGD (SEQ ID NO: 1) to different cell types. Tests included EPCs/ECs from different sources, including HECFCs (A), HCAECs (B), HMVECs (C), and THP-1 monocytes (D), Platelets (E), as well as K562 cells engineered to highly express αvβ3 (αvβ3-K562, F), and αIIbβ3 (αIIbβ3-K562, G). Cells were incubated with the LXW7-bio, GRGD-bio (SEQ ID NO: 1), or D-Biotin peptide and subsequently incubated with streptavidin-phycoerythrin. Flow cytometry analysis was performed to determine the binding affinity of the ligands. Samples treated with D-biotin were used as negative controls.

Conventional tri-amino acid sequence, arginine-glycine-aspartate, or "RGD" has been widely used as an adhesive peptide in the biomaterials field to improve cell attachment. However, conventional RGD binds to numerous types of cells and does not have specific binding affinity to EPCs/ECs (Barber et al. (2007) *J Biomed Mat Res* 80:306; Hynes (2002) *Cell* 110:673; Rammelt et al. (2006) *Biomaterials* 27:5561). To investigate whether LXW7 possess higher specificity to EPCs/ECs, we compared EC binding specificity and affinity of LXW7 with that of conventional GRGD peptide (SEQ ID NO: 1) by flow cytometry. The results showed that LXW7 had higher binding affinity with different types of EPCs/ECs than conventional GRGD peptide (SEQ ID NO: 1) (FIG. 10, A-C). Both ligands did not bind to THP-1 monocytes (FIG. 10, D). Consistent with our previous results, LXW7 had very low binding affinity with platelets but GRGD (SEQ ID NO: 1) showed strong binding to platelets (FIG. 10, E). To confirm whether the ligands were indeed targeting integrin αvβ3, we used αvβ3-K562 cells that highly express integrin αvβ3 to test their binding affinity to GRGD (SEQ ID NO: 1) and LXW7. We found that LXW7 had higher binding affinity than GRGD (SEQ ID NO: 1), although both GRGD (SEQ ID NO: 1) and LXW7 bound well to αvβ3-K562 cells (FIG. 10, F).

Expression of integrin αIIbβ3 is restricted to cells of the megakaryocyte lineage, such as platelets, and it has been shown that αIIbβ3-mediated formation of platelet aggregates causes thrombosis in circulation (Bennett (2005) *J Clinical Investigation* 115:3363; Lefkovits et al. (1995) *New England J Med* 332:1553). To investigate whether the ligands bound to platelets that can cause thrombosis in vivo, we employed αIIbβ3-K562 cells that were engineered to highly express αIIbβ3 on their surface. We found that LXW7 showed very low binding to αIIbβ3-K562 cells whereas GRGD (SEQ ID NO: 1) showed very strong binding (FIG. 10, G).

These results demonstrated that LXW7 possesses higher binding affinity to integrin αvβ3 but lower binding affinity to integrin αIIbβ3 than conventional RGD peptide. This indicates that LXW7 has superior potential than the conventional RGD peptide with respect to its ability to support stronger and more specific EPC/EC binding.

Figure 11:
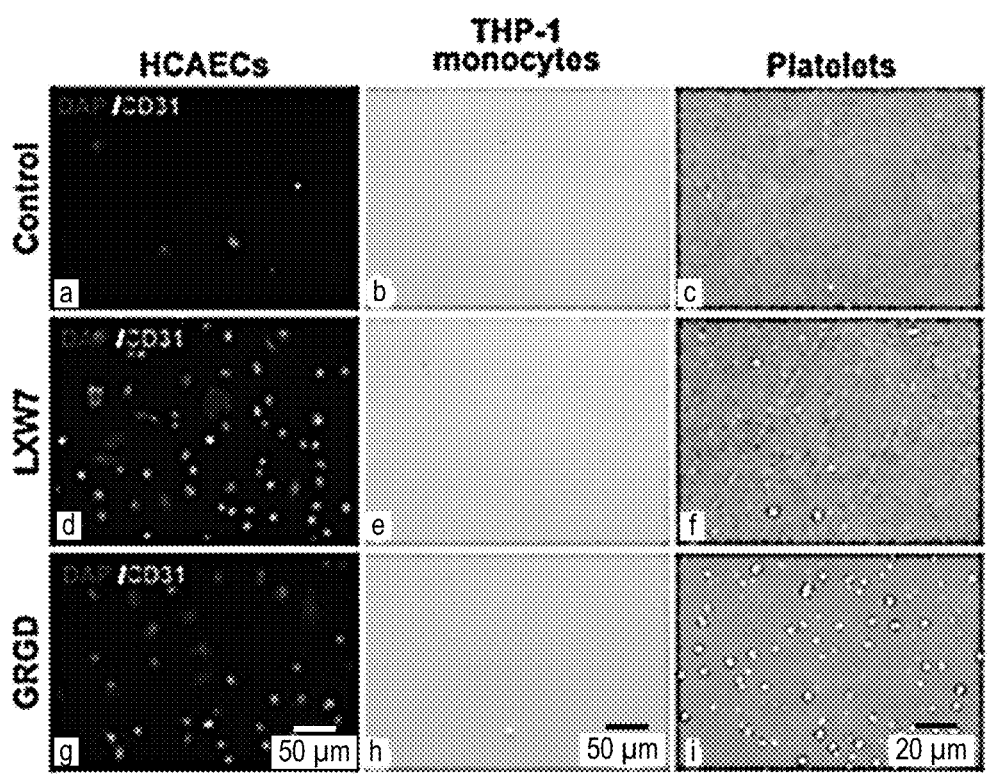
FIG. 11 presents images from an assay of attachment of cells and platelets to LXW7 and GRGD (SEQ ID NO: 1) treated surfaces. The images are of attached HCAECs (left panels), THP-1 monocytes (middle panels) and platelets (right panels) on surfaces treated by D-Biotin (a-c) (control), LXW7 (d-f) or GRGD (g-i) (SEQ ID NO: 1). Scale bars for a, b, d, e, g and h are 50 µm. Scale bars for c, f and i are 20 µm.
Figure 12:
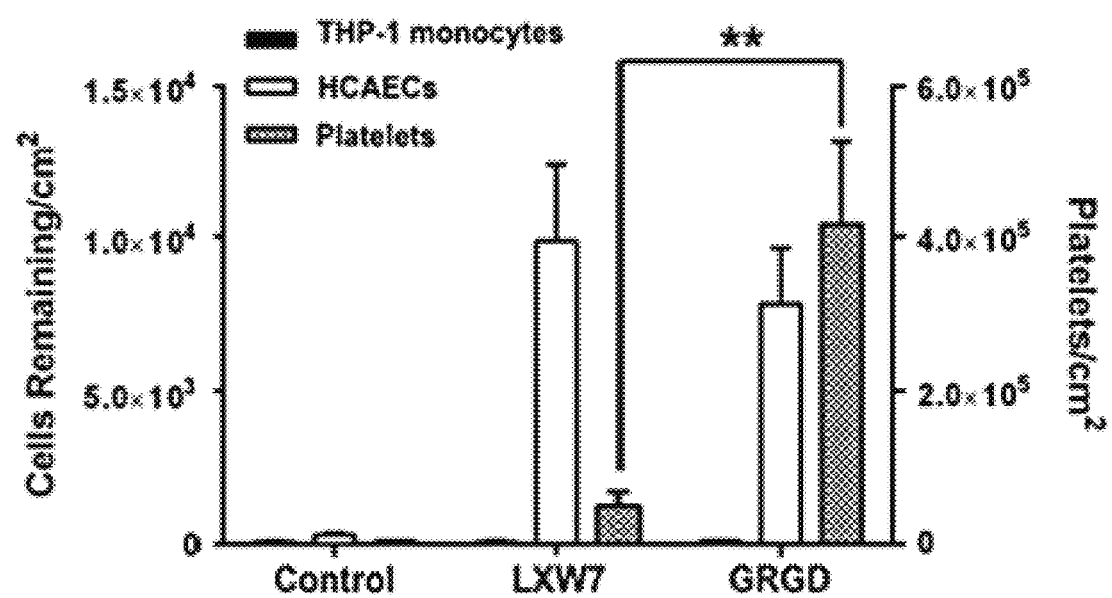
FIG. 12 is a graph of results from the attachment assay of FIG. 11. The number of cells or platelets attached on different treated surfaces were quantified and statistical analyses were performed. Data were expressed as mean±standard deviation: **p<0.01 (n=4).

To confirm the results from the flow cytometry analysis, we employed live cell culture assays to determine cell-ligand binding affinity. We used LXW7-bio or GRGD-bio (SEQ ID NO: 1) (D-biotin as the negative control) to treat the culture surfaces and investigated selective attachment of HCAECs, THP-1 monocytes, and platelets on culture surfaces. HCAECs bound to both LXW7 and GRGD (SEQ ID NO: 1) treated surfaces within 10 minutes (FIG. 11, d and g) but not to the control surface (FIG. 11, a). The number of attached cells were quantified and showed that LXW7 treated surface attracted more HCAECs than the GRGD-modified (SEQ ID NO: 1) surface (FIG. 12), further confirming that LXW7 outperforms GRGD (SEQ ID NO: 1) in regards to binding with ECs. Additionally, both LXW7 and GRGD (SEQ ID NO: 1) treated surfaces did not support THP-1 monocyte attachment (FIG. 11, b, e and h and FIG. 12). Furthermore, LXW7 treated surface showed limited platelet adhesion whereas GRGD (SEQ ID NO: 1) treated surface allowed a significantly higher number of platelets to attach (FIG. 11, c, f and i and FIG. 12). This further confirmed our previous results that LXW7 supported stronger EC attachment but significantly weaker platelet attachment than conventional GRGD peptide (SEQ ID NO: 1).

Example 14. Ability of LXW7 to Improve EC Biological Functions

Figure 13:
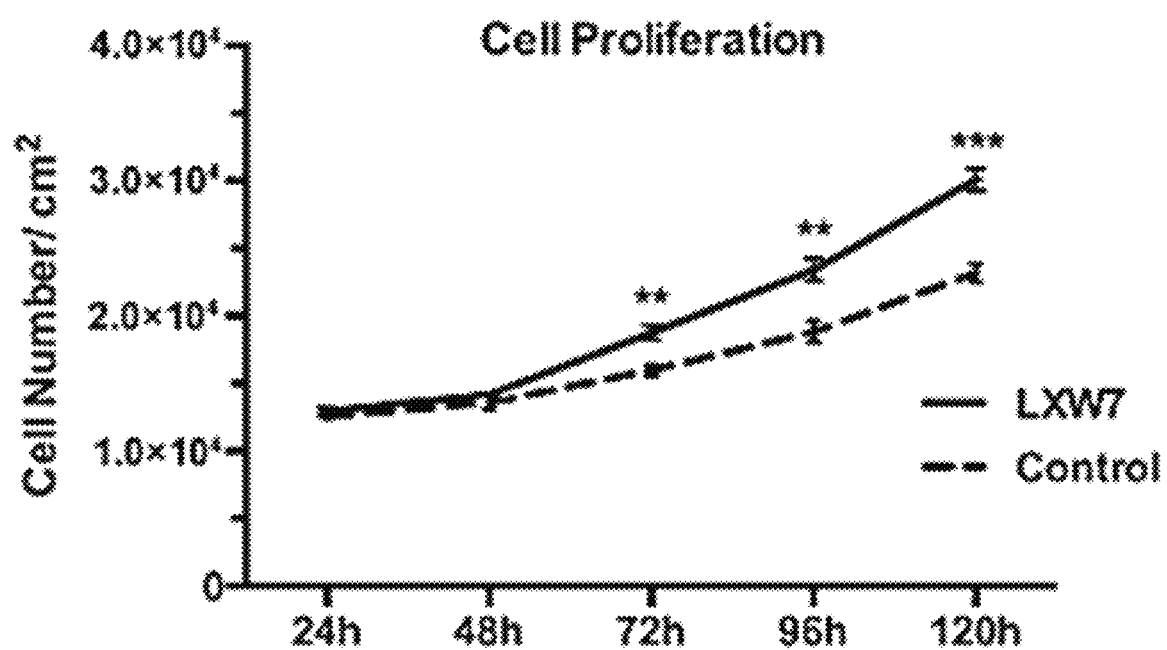
FIG. 13 is a graph showing proliferation of ECs on LXW7 treated surfaces and D-biotin treated surface (control) as assessed by an MTS assay. Data were expressed as mean±standard deviation: p<0.01, *p<0.001 (n=4).
Figure 14:
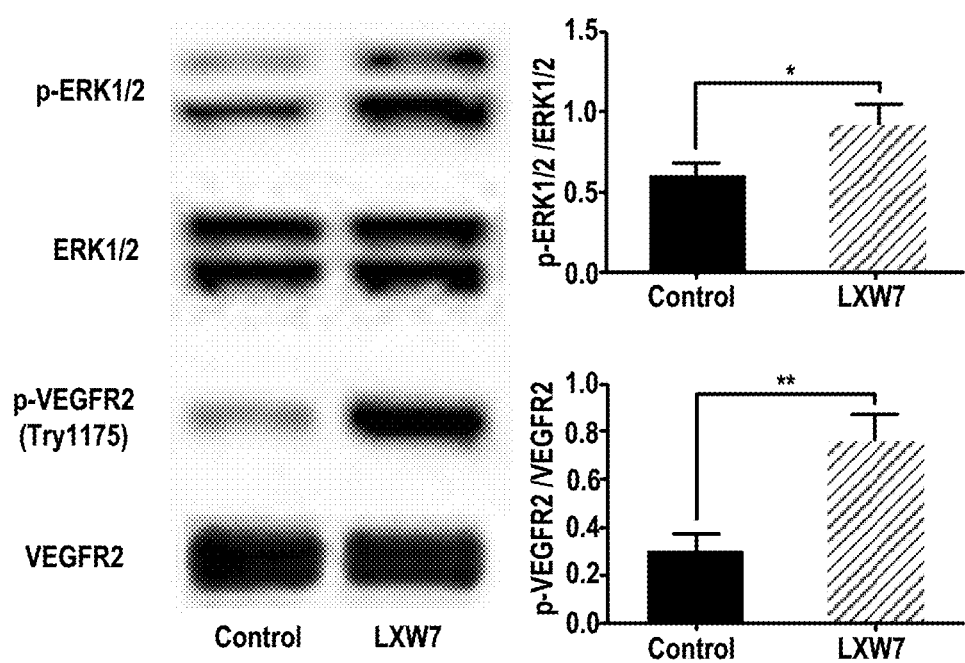
FIG. 14 presents additional data showing the effects of LXW7 on EC biological functions. Shown are results from Western-blot analysis (left panels) and densitometry measurements (right panels) of the effect of LXW7 on phosphorylation of VEGFR2 (Tyr1175) and phosphorylation of ERK1/2. Data were expressed as mean±standard deviation: *p<0.05, **p<0.01 (n=4).
Figure 15:
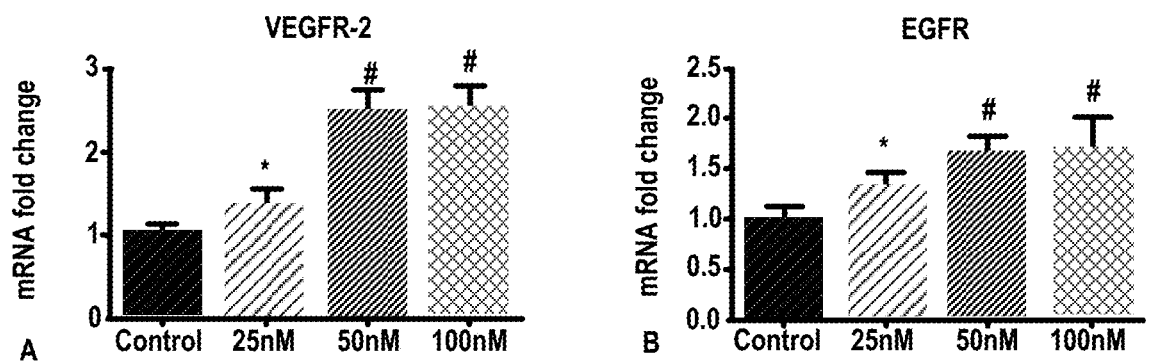
FIG. 15 presents graphs of mRNA levels of VEGFR-2 (A) and EGFR (B) on EPCs after treating with different concentrations of LXW7 for 48 h. *P<0.05 vs. Control, #P<0.05 vs. 25 nM (n=10 per group).

The effect of LXW7 on ECs proliferation was tested by MTS assay at different time points. Results showed that when compared with the D-biotin treated surface (control), the LXW7 treated surface significantly promoted EC proliferation after 48 hours in culture, and that this trend was maintained for the entire period of the experiment (FIG. 13). ECs cultured on LXW7 treated surface for 96 hours were collected for Western-blot analysis. When compared with the D-biotin treated surface (control), the LXW7 treated surface significantly increased the phosphorylation of VEGFR2 (Tyr1175) and phosphorylation of its downstream signaling molecule ERK1/2 in ECs (FIG. 14). Also, increases in VEGFR2 and EGFR mRNA levels were found to be dependent on treatment time with LXW7 (FIG. 15). Without being bound to any particular theory, LXW7 induced EC proliferation may be attributed to the fact that LXW7 activated integrin αvβ3, and therefore enhanced phosphorylation of VEGFR2 and ERK1/2 and induced EC proliferation.

Example 15. Modification of Biomaterial Scaffold Surface with LXW7

Figure 16:
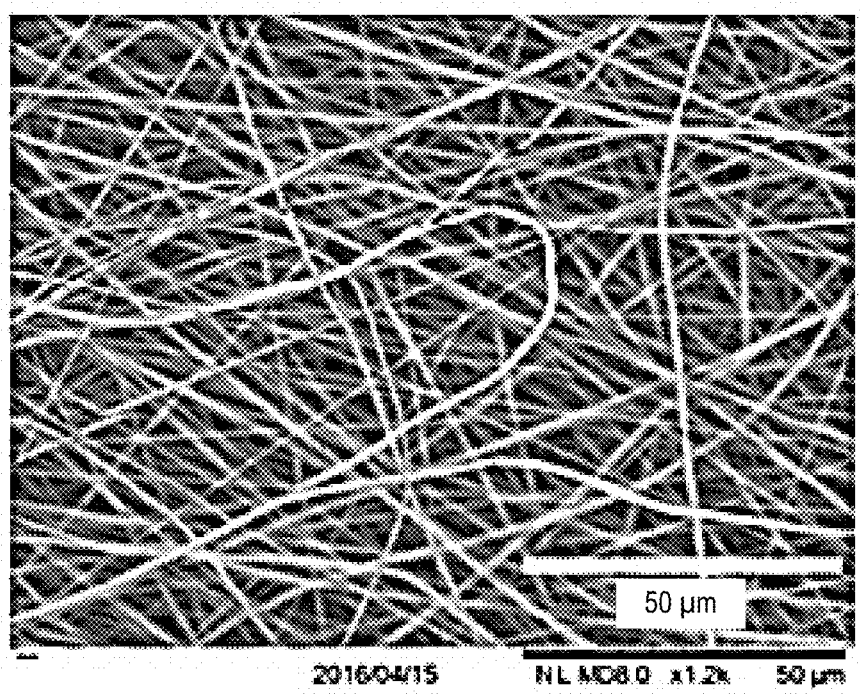
FIG. 16 is an image from an SEM analysis of the structure of an electrospun microfibrous scaffold modified with LXW7 by Click chemistry.
Figure 17:
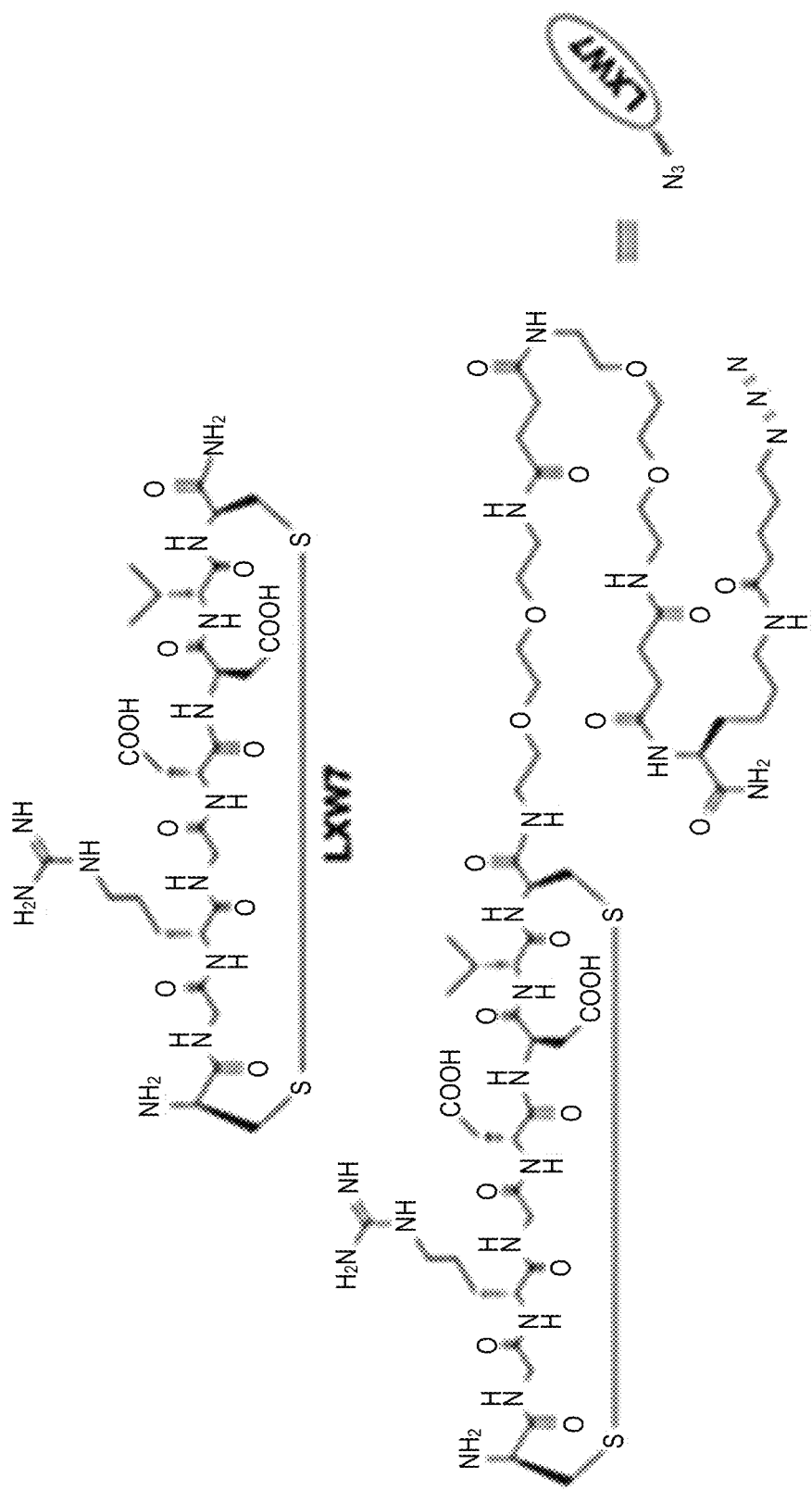
FIG. 17 shows the chemical structures of LXW7 and LXW7-N$_3$.
Figure 18:
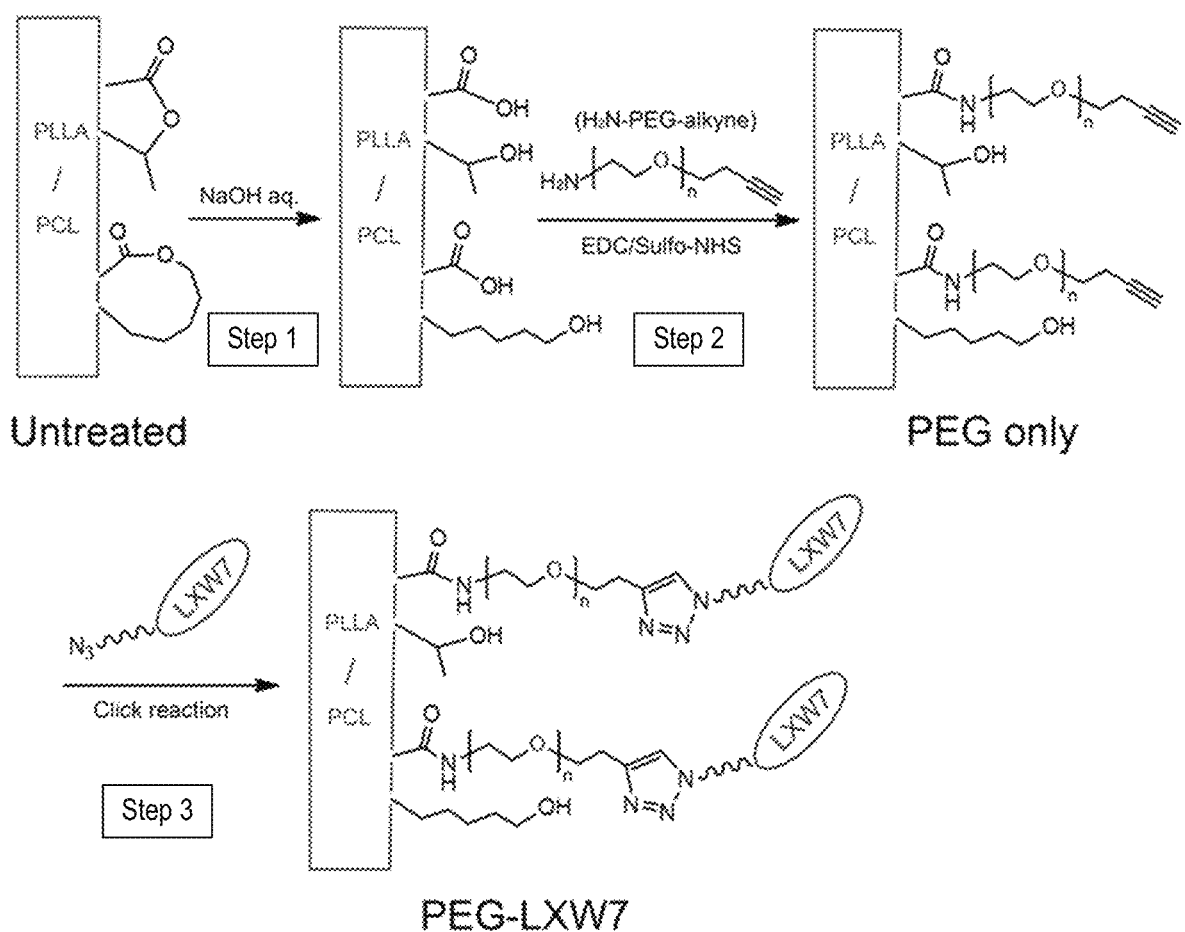
FIG. 18 presents a schematic of the chemical process involved in the linking of LXW7 to the electrospun microfibrous scaffold surface.
Figure 19:
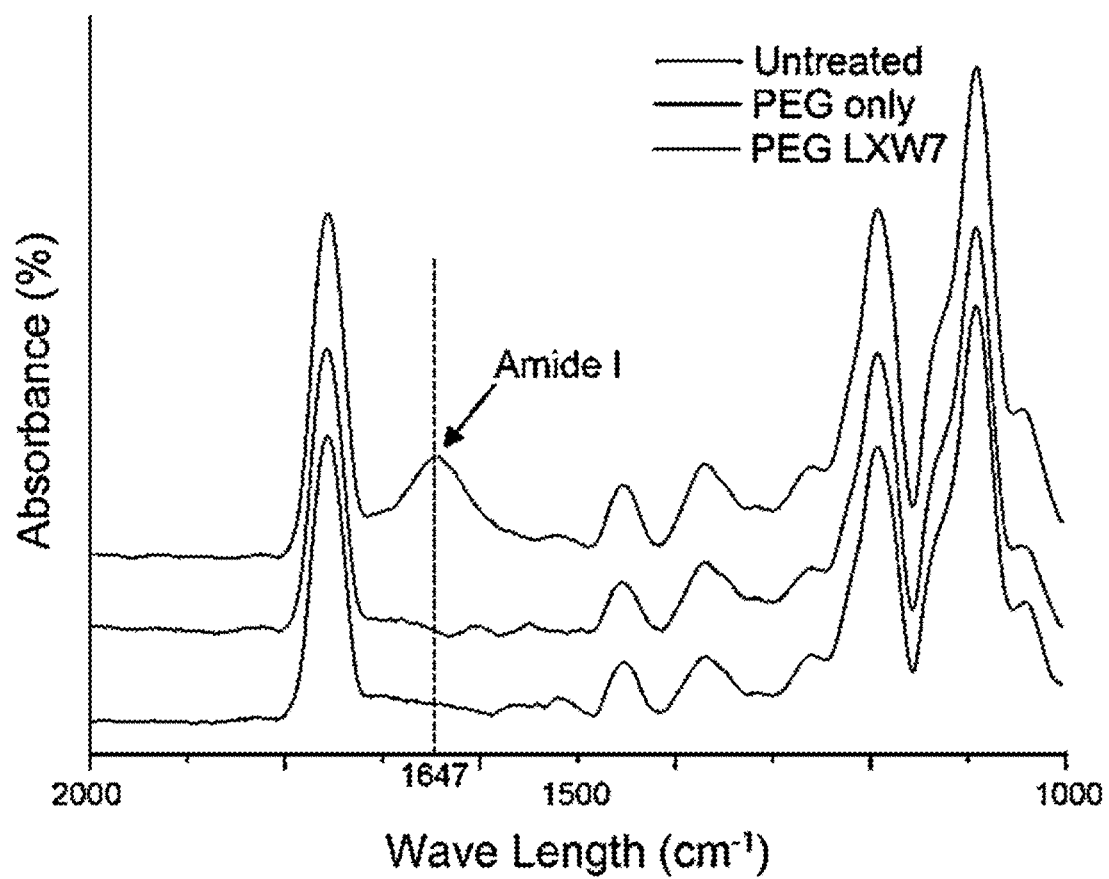
FIG. 19 is a graph of ATR-FTIR spectra of membranes with untreated, PEG only modified, and PEG-LXW7 modified scaffolds.

ECM provides a three-dimensional structure and native ligands for cell attachment and tissue growth and functions (Wang et al. (2009) *Nat Rev* 10:75). To mimic ECM structure, we employed electrospinning technology to produce microfibrous scaffolds using PLLA and PCL polymer blends. SEM images showed that the electrospun scaffolds had a porous structure of microfibers (FIG. 16), similar in morphology to the native ECM. These scaffolds have a disadvantage over the ECM in that they lack bioactive motifs such as the integrin ligands that are normally present on the ECM and hence modification of the artificial ECM with functional ligands could improve its biological functions. To improve biological functions of the microfibrous scaffolds, we developed a protocol to functionalize the polymer surface by LXW7 via Click chemistry (FIG. 18). LXW7 was first functionalized with an azide group (FIG. 17). Microfibrous membranes were functionalized with PEG by using $H_2N$-PEG-alkyne. $H_2N$-PEG-alkyne was covalently attached to the carboxylic groups on the microfibers using EDC and Sulfo-NHS (FIG. 18). LXW-$N_3$ was then attached to $H_2N$-PEG-alkyne functionalized microfibers by Click chemistry (FIG. 18). ATR-FTIR spectrum analysis which has been proven to be a powerful tool for detecting amide bonds on solid surfaces (Lin et al. (2001) *Artificial Organs* 25:617) was used in this study to confirm the immobilization of LXW7 on the scaffold surface. The ATR-FTIR spectra of the untreated and modified surfaces are shown in FIG. 19. The typical spectrum of the membranes modified with PEG-LXW7 was represented by an obvious rise in the intensity of the peak attributed to the amide I groups (1647 $cm^{-1}$), which were distributed in a large number in the structure of LXW7-$N_3$ (FIG. 17). The spectrum of the membranes modified by PEG only showed only a small evolution around 1630 and 1670 $cm^{-1}$ when compared to the spectrum of the untreated membrane, because only a few amide I groups were formed after the membranes were modified with PEG linker only (FIG. 18). There was a significant difference between the spectra of PEG-LXW7 and PEG only modified membranes at 1647 $cm^{-1}$, indicating that a large amount of amide I groups were introduced onto the membrane after LXW7 was modified (FIG. 19). All these data confirmed that LXW7 had been successfully immobilized on the membrane surface.

Example 16. EC Attachment and Spreading Supported by Biomaterial Scaffold Surface Modified with LXW7

Figure 20:
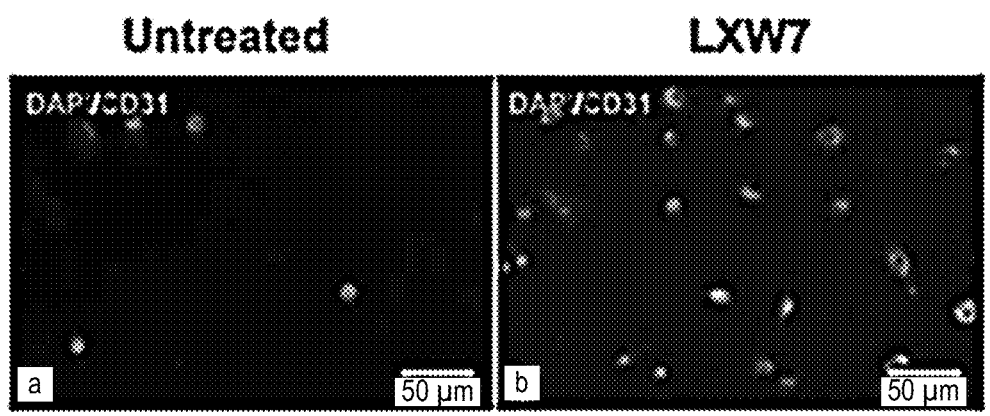
FIG. 20 presents representative immunocytochemistry images of CD31 stained HCAECs adhered on untreated nanofibrous membrane surface (a) and LXW7-modified nanofibrous membrane surface (b) after 2 hours incubation. Scale bar=50 µm.
Figure 21:
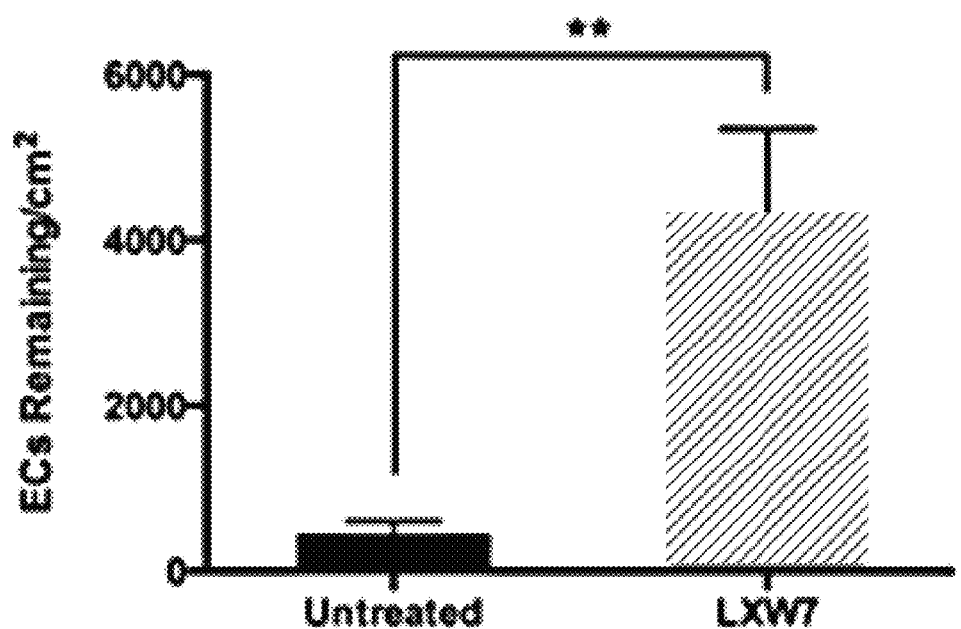
FIG. 21 is a graph of the quantification and correlative statistical analysis of adhered cells from the CD31 immunostaining images of FIG. 20. Data were expressed as mean±standard deviation: **$p<0.01$ (n=3).
Figure 22:
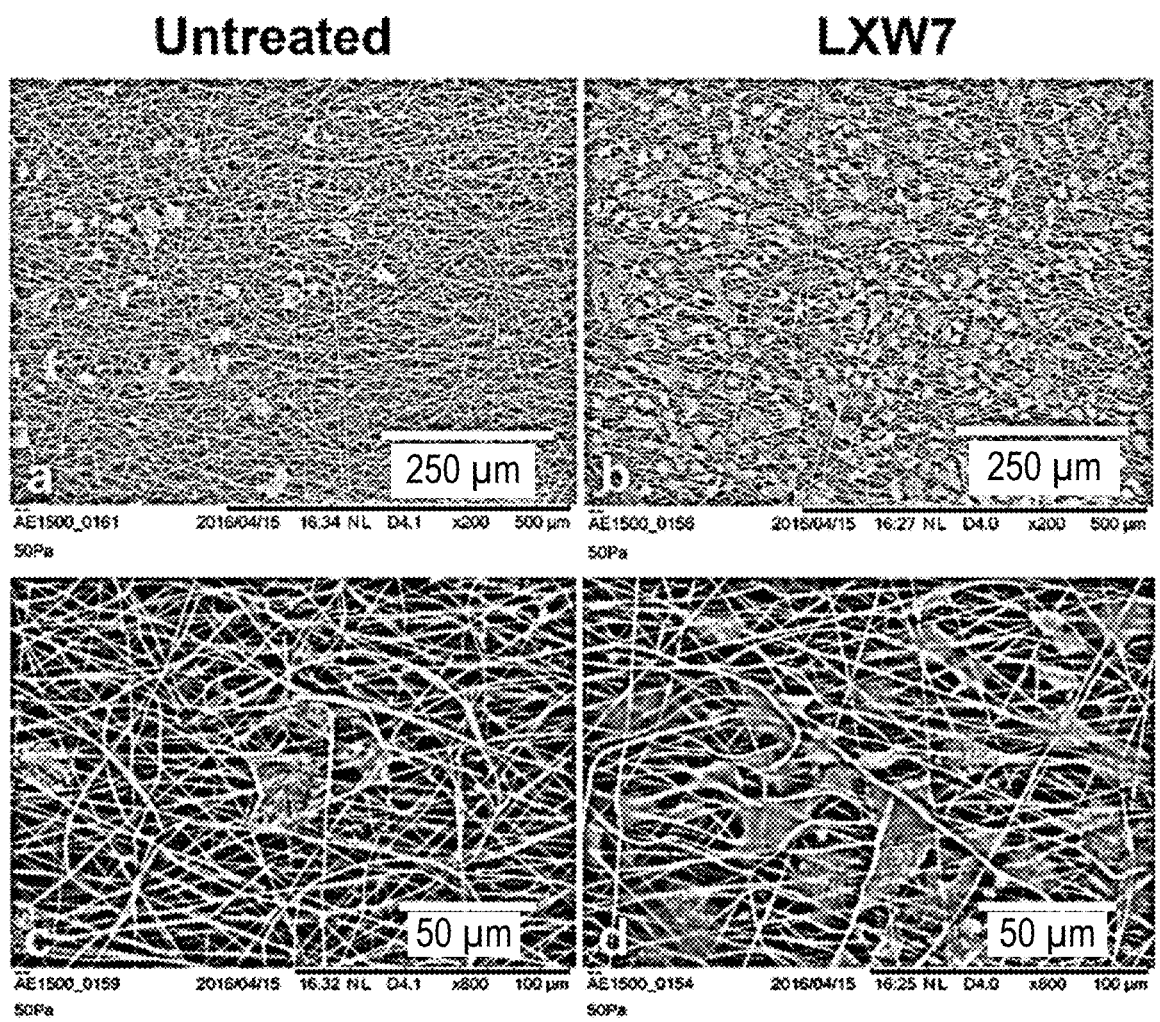
FIG. 22 presents SEM images of ECs grown on untreated membrane surface (a, c) and LXW7-modified nanofibrous membrane surface (b, d) for 2 days (scale bars in a, b: 250 μm, c, d: 50 μm).
Figure 23:
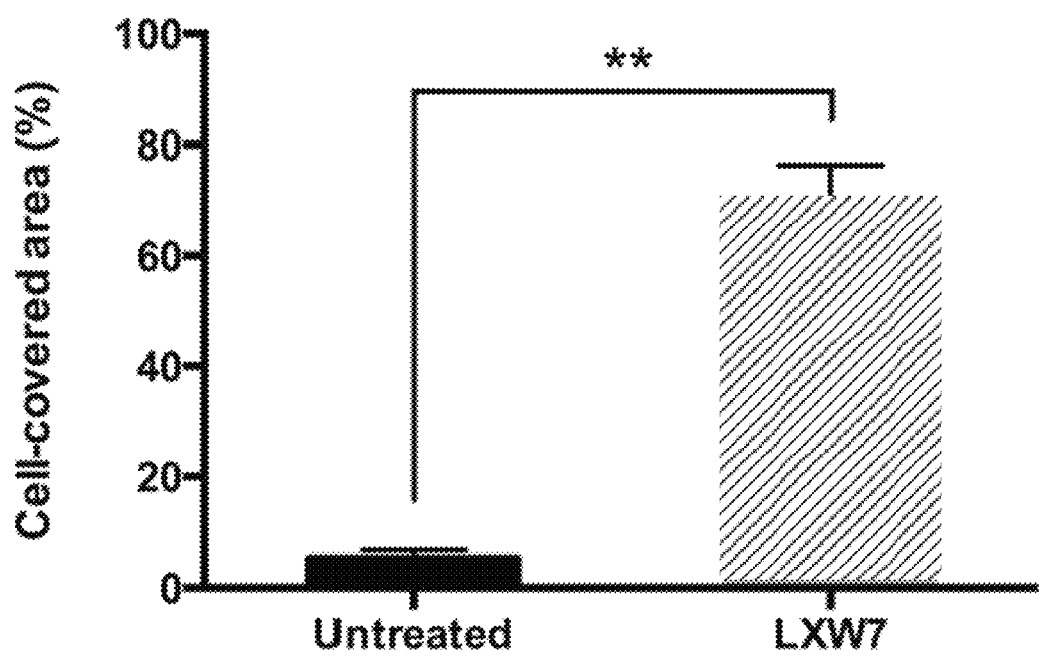
FIG. 23 is a graph of the quantification and correlative statistical analysis of cell-covered area from the SEM images of FIG. 22. Data were expressed as mean±standard deviation: **$p<0.01$ (n=3).

HCAECs were seeded on PLLA/PCL microfibrous membranes modified with or without LXW7 and cultured in EGM-2 media for 2 hours. After washing, HCAECs attached on LXW7 modified membrane (FIG. 20, b) and untreated membrane (FIG. 20, a) were fixed and stained with CD31 antibody. Quantification of CD31 positive cells showed that there were significantly more HCAECs adhered to LXW7-modified membranes when compared to untreated membranes (FIG. 21). HCAECs adhered on the membrane surfaces at 2 hours were kept in culture for two days. SEM analysis showed that ECs grew and spread much better on LXW7-modified membrane (FIG. 22, b and d) compared to the untreated membrane (FIG. 22, a and c). Quantification of cell-covered area showed that there was significant more cell-covered area on LXW7-modified membranes when compared to that on untreated membranes (FIG. 23). These results demonstrated that the function of LXW7 was well maintained after chemical modification and LXW7-modified biomaterials supported excellent attachment and spreading of ECs.

Example 17. In Vivo Evaluation of Vascular Grafts

To test the ability of LXW7 to promote endothelialization, polymer-based small diameter vascular grafts (ID 1 mm) were functionalized with LXW7 via Click chemistry and evaluated in a rat carotid artery bypass model. Male Sprague-Dawley rats (weight, 350-400 g) were purchased from the Charles River animal facility. The rats were anesthetized with 2.0% isoflurane and their core body temperature was maintained at 37.5° C. using a heating pad. The left common carotid artery of rat was dissected freely and clamped at the proximal and distal ends. After cutting the common carotid artery, the graft was performed with an end to end anastomosis by using a 10-0 needle, and circulation was restored after careful de-airing. At different time points for up to 6 weeks, the rats were euthanized to check the patency of the graft. The animals were then sacrificed and the vascular grafts were explanted. Histological analysis of the cross sections of the grafts was used to confirm the patency.

Samples for histological examination were snap-frozen in optimal cutting temperature (OCT) compound, and sectioned into 10-μm thickness using cryostat. Immunohistochemical staining was used to analyze the tissue sections with CD31 (550300, mouse, BD Biosciences) and CD34 (AF4117, rat, R&D) primary antibodies. Immunohistochemistry images were captured with a Canon confocal microscope.

The grafts were explanted and fixed with 4% paraformaldehyde for 30 minutes. Each graft was cut into 4 slices longitudinally by using microscissors. The samples were washed with PBS, blocked with 1% bovine serum albumin, and incubated with primary antibodies against EPC marker CD34, EC marker CD31 and then incubated with Alexa-Fluor 488 or Alexa-Fluor 546 labeled secondary antibodies, followed by confocal microscopy.

Figure 24:
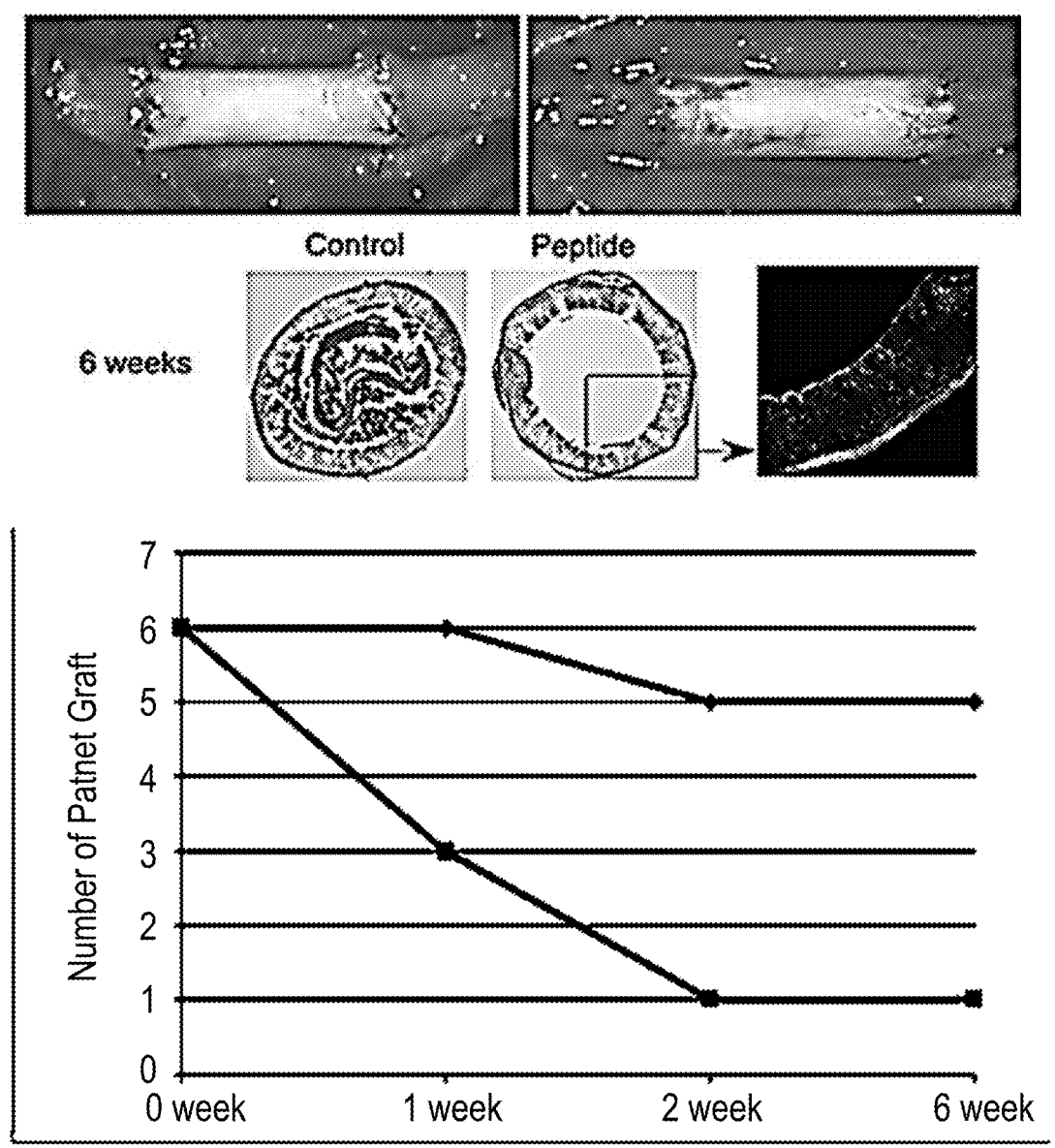
FIG. 24 presents results from examinations of explanted grafts. Shown are images of new capillary formation surrounding the outer side of untreated graft and LXW7 treated graft at 6 weeks after implantation. Also shown is an immunostained image of cross sections of LXW7 treated graft for endothelial cell (EC) marker CD31. The displayed graph plots the patency of grafts at various time points, with each group at each time point including 6 animals.
Figure 25:
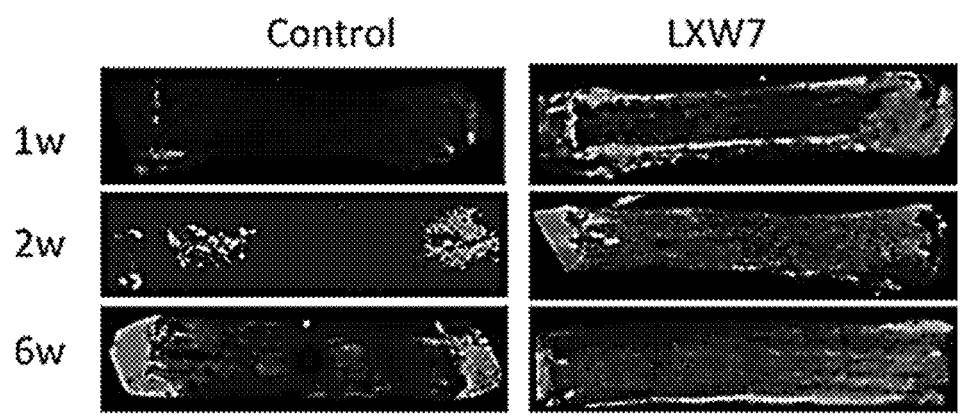
FIG. 25 presents images of en face DAPI staining of the luminal surface of the explanted grafts of FIG. 24. DAPI staining shows that there were fewer cells on the luminal surface of the control grafts (left panels) than the LXW7 treated grafts (right panels). Three time points after implantation were compared side by side (1 week, 2 weeks, 6 weeks).
Figure 26:
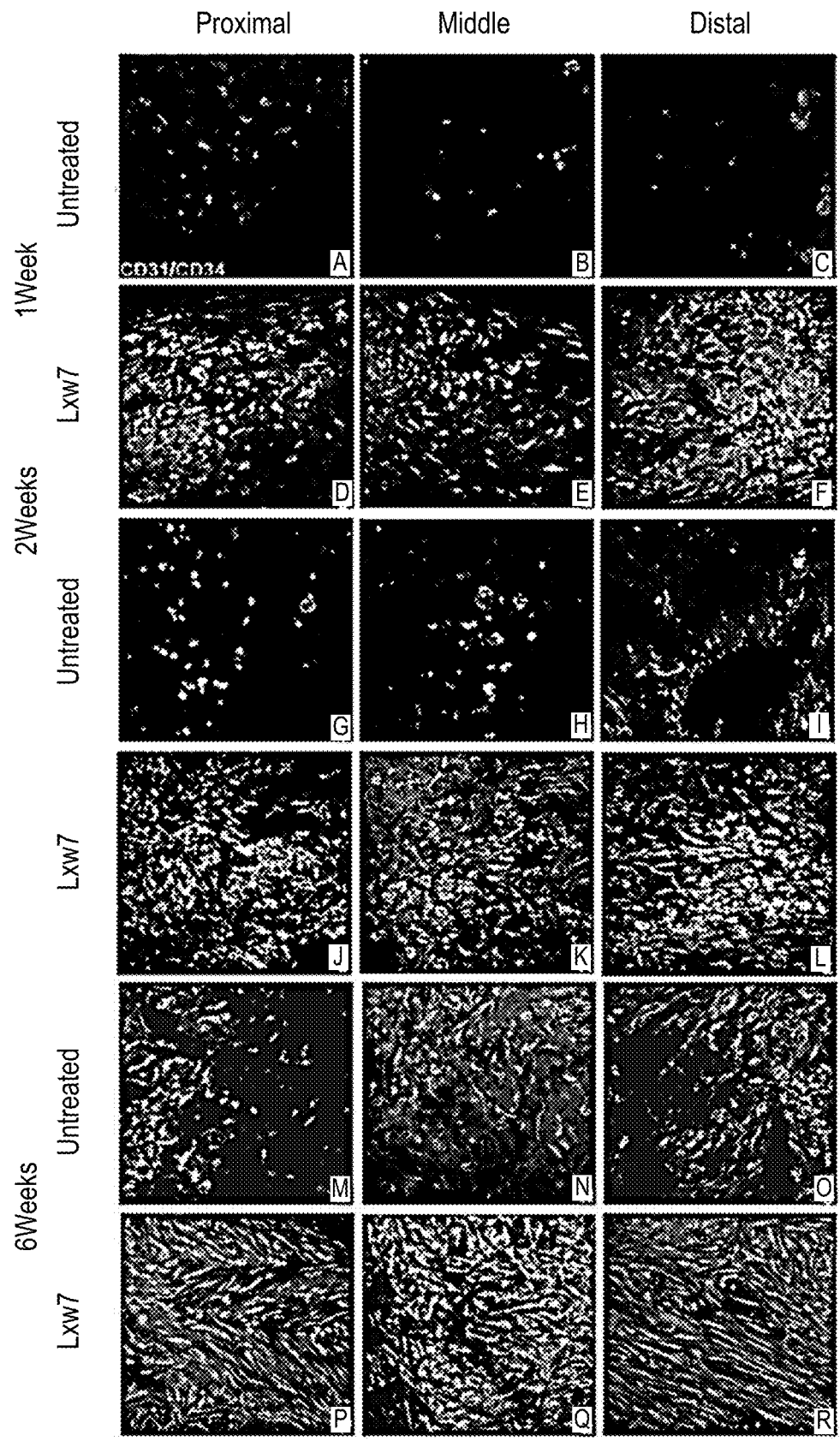
FIG. 26 presents images of en face immunostaining for CD31 and CD34 of proximal, middle and distal portions of grafts. Untreated grafts (A-C), LXW7 treated grafts (D-F) at 1 week after implantation. (G-L) Untreated grafts (G-I), LXW7 treated grafts (J-L) at 2 week after implantation. (M-R) Untreated grafts (M-O), LXW7 treated grafts (P-R) at 6 week after implantation

Results from the above examinations of explanted grafts are presented in FIG. 24, FIG. 25, and FIG. 26. The LXW7-modified grafts were found to have a significantly higher patency rate than the control grafts. After 6 weeks post implantation, 5 out of 6 LXW7-modified grafts were patent versus only 1 out of 6 control grafts was patent (FIG. 24). At 6 weeks, mature ECs were present throughout the whole length of the LXW7-modified grafts while only a limited number of ECs were identified in the middle segment of the control grafts (FIG. 26). This confirms that LXW7 coating on the luminal surface of synthetic vascular grafts can generate a "living" endothelium.

Although the foregoing invention has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

IX. Exemplary Embodiments

Exemplary embodiments provided in accordance with the presently disclosed subject matter include, but are not limited to, the claims and the following embodiments:

1. A scaffold comprising: a polymer; and a peptide ligand covalently immobilized on the surface of the polymer, wherein the peptide ligand increases the attachment of endothelial cells and/or endothelial progenitor cells to the scaffold, and wherein the peptide ligand is a compound of Formula I:

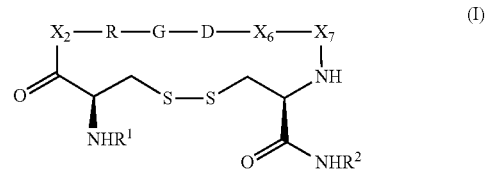

wherein $X_2$, $X_6$, and $X_7$ are each independently an amino acid, wherein at least one of $X_2$, $X_6$, and $X_7$ is a D-amino acid; le is selected from the group consisting of H, $C_{1-6}$ alkyl, —C(O)$R^{1a}$, and L-A; $R^{1a}$ is selected from the group consisting of $C_{1-6}$ alkyl, $C_{1-6}$ heteroalkyl, $C_{1-6}$ alkyl-NH$_2$, $C_{1-6}$ alkyl-C(O)N(H)—$C_{1-6}$ heteroalkyl, cycloalkyl, $C_{1-6}$ alkyl-cycloalkyl, heterocycloalkyl, $C_{1-6}$ alkyl-heterocycloalkyl, aryl, $C_{1-6}$ alkyl-aryl, heteroaryl, and $C_{1-6}$ alkyl-heteroaryl, wherein the cycloalkyl, heterocycloalkyl, heteroaryl, and aryl groups are optionally substituted with a member selected from the group consisting of halogen, —NO$_2$, —OH, —CN, $C_{1-6}$ alkyl, $C_{1-6}$ alkoxy, $C_{1-6}$ haloalkyl, and $C_{1-6}$ haloalkoxy; $R^2$ is selected from the group consisting of H, $C_{1-6}$ alkyl, and L-A; L is a linker; and A is an active agent.

2. The scaffold of embodiment 1, wherein $R^1$ and $R^2$ are each independently selected from the group consisting of H, $C_{1-6}$ alkyl and L-A; L is a linker; A is an active agent; $X_2$ is selected from the group consisting of Gly, Ala, Sar and f3-alanine, and stereoisomers thereof; $X_6$ is selected from the group consisting of Val, Leu, Ile, Met, Phe, Asn, Glu, Gln, His, Lys, Arg, Asp, Gly, Ala, Ser, Thr, Tyr, Trp, Pro, Aad, Bec, Bmc, Bmp, Phe(4COOH), Hyp, HoSer, Tha, Ahch, Actp, Akch, Tyr(diI), Trp, Thz, 2Thi, 3Thi, Cit, HoCit, Aib, Nglu, and Fua, and stereoisomers thereof; and $X_7$ is selected from the group consisting of Val, Leu, Ile, Met, Phe, Asn, Glu, Gln, His, Lys, Arg, Asp, Gly, Ala, Ser, Thr, Tyr, Trp, Pro, Bmp, HoSer, Nglu, HoCit, Bec, Aad, Hyp, Ahch, Phe(4COOH), Akch, Aecc, Abu, Phe(3,4-diOMe), Cpa, 2-Thi, Thz, Phg, Phe(4-NO$_2$), Nle, (NMe)Phe, Aic, Chg, Bta, Bpa, Nal2, Nal1, Tic, Ppca, Cha, Bipa, Deg, Dpg, Acpc, Bmc, Cit, Sar, Tha, Pra, Actp, Aib, Agl, Acbc, Fua, Nva, Thi, Trp, Bug, Ach, (NMe)Val, Cpeg, (CαMe)Phe, Tyr(diI), Phe(2-Cl), Bua, HoPhe, HoLeu, Sta, Ing, Phe(4-CF$_3$), Oic, Dpa, Phe(4-t-Bu), HoCha and Phe(3,4-diCl), and stereoisomers thereof.

3. The scaffold of embodiment 1, wherein the peptide ligand is a compound of Formula Ia:

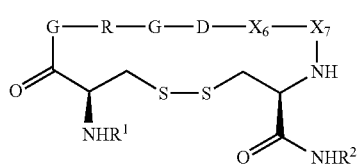

(Ia)

wherein $X_6$ and $X_7$ are each independently a D-amino acid; $R^1$ is selected from the group consisting of H, $C_{1-6}$ alkyl, and —C(O)$R^{1a}$; $R^{1a}$ is selected from the group consisting of $C_{1-6}$ alkyl, $C_{1-6}$ heteroalkyl, $C_{1-6}$ alkyl-$NH_2$, $C_{1-6}$ alkyl-C(O)N(H)—$C_{1-6}$ heteroalkyl, cycloalkyl, $C_{1-6}$ alkyl-cycloalkyl, heterocycloalkyl, $C_{1-6}$ alkyl-heterocycloalkyl, aryl, $C_{1-6}$ alkyl-aryl, heteroaryl, and $C_{1-6}$ alkyl-heteroaryl, wherein the cycloalkyl, heterocycloalkyl, heteroaryl and aryl groups are optionally substituted with a member selected from the group consisting of halogen, —$NO_2$, —OH, —CN, $C_{1-6}$ alkyl, $C_{1-6}$ alkoxy, $C_{1-6}$ haloalkyl and $C_{1-6}$ haloalkoxy; and $R^2$ is selected from the group consisting of H and $C_{1-6}$ alkyl.

4. The scaffold of embodiment 3, wherein $R^1$ and $R^2$ are each independently selected from the group consisting of H and $C_{1-6}$ alkyl.

5. The scaffold of embodiment 3, wherein $X_6$ is selected from the group consisting of DSer, DAsp, DGlu, and DCit; and $X_7$ is selected from the group consisting of DPhe, DGlu, DSer, DBug, DBta, DVal, DAgl, DPra, D(NMe)Val, D(CαMe)Val, DAbu, DIng, DIle, DTha, DAsp, and DNal1.

6. The scaffold of embodiment 3, wherein $X_6$ is selected from the group consisting of DAsp and DSer; and $X_7$ is selected from the group consisting of DGlu, DPhe, DSer, DVal, DBug and DBta.

7. The scaffold of embodiment 3, wherein the peptide ligand is selected from the group consisting of cGRGDsfc, cGRGDdfc, cGRGDsec, cGRGDdsc, cGRGDd-DBug-c, cGRGDd-DBta-c, cGRGDdvc, Ac-cGRGDdvc, (β-alanine)-cGRGDdvc, (Ebes)-cGRGDdvc, cGRGDd-DAgl-c, cGRGDd-DPra-c, cGRGDd-DBug-c, cGRGDd-D(NMe)Val-c, cGRGDd-D(CαMe)Val-c, cGRGDd-DAbu-c, cGRGDd-DNal1-c, cGRGDd-DNal2-c, and cGRGDd-DBta-c.

8. The scaffold of embodiment 3, wherein the peptide ligand is selected from the group consisting of cGRGDsfc, cGRGDdfc, cGRGDsec, cGRGDdsc, cGRGDdvc, cGRGDd-DBug-c and cGRGDd-DBta-c.

9. The scaffold of embodiment 3, wherein the peptide ligand is cGRGDdvc (LXW7).

10. The scaffold of any one of embodiments 1-9, wherein the peptide ligand binds to integrin αvβ3 on the cells.

11. The scaffold of any one of embodiments 1-10, wherein the polymer is selected from the group consisting of poly (L-lactic acid) (PLLA), polycaprolactone (PCL), poly (lactic-co-glycolic acid) (PLGA), hydroxyapatite (HA), poly (lactide-co-ε-caprolactone) (PLCL), polytetrafluoroethylene (PTFE), expanded polytetrafluoroethylene (ePTFE), and combinations thereof.

12. The scaffold of any one of embodiments 1-11, wherein the polymer further comprises a coating, and wherein the peptide ligand is covalently attached to the coating.

13. The scaffold of embodiment 12, wherein the coating is a parylene polymer.

14. The scaffold of any one of embodiments 1-13, wherein endothelial cells, endothelial progenitor cells, and/or osteogenic cells are seeded on the scaffold.

15. An engineered tissue comprising the scaffold of any one of embodiments 1-14.

16. A coating comprising: a coating polymer; and the peptide ligand of any one of embodiments 1-9, wherein the peptide ligand is covalently attached to the coating polymer.

17. The coating of embodiment 16, wherein the peptide ligand is cGRGDdvc (LXW7).

18. The coating of embodiment 16 or 17, wherein the coating polymer is a parylene polymer.

19. A method for improving endothelialization and vascularization of endothelial cells and/or endothelial progenitor cells for tissue regeneration in a subject, the method comprising implanting the scaffold of any one of embodiments 1-14 into the subject.

20. The method of embodiment 19, wherein the peptide ligand increases the recruitment of endothelial cells and/or endothelial progenitor cells to the scaffold.

21. The method of embodiment 19 or 20, wherein the peptide ligand increases the proliferation of endothelial cells and/or endothelial progenitor cells on the scaffold.

22. A method for repairing a bone defect in a subject, the method comprising implanting the scaffold of any one of embodiments 1-13 into the subject.

23. The method of embodiment 22, wherein endothelial cells and osteogenic cells are seeded on the scaffold prior to implantation.

24. A method of coating a surface, the method comprising: functionalizing a coating polymer; adhering the coating polymer to the surface; and covalently attaching a peptide ligand to the coating polymer, wherein the peptide ligand is the peptide ligand of any one of embodiments 1-9 or a functionalized derivative thereof.

25. The method of embodiment 24, wherein the peptide ligand is cGRGDdvc (LXW7) or a functionalized derivative thereof.

26. The method of embodiment 24 or 25, wherein the coating polymer is a parylene polymer.

27. The method of any one of embodiments 24-26, wherein the functionalizing of the coating polymer includes introducing alkyne functional groups to the coating polymer.

28. The method of embodiment 27, wherein the peptide ligand is functionalized with an azide functional group.

29. The method of any one of embodiments 24-28, wherein the surface comprises a scaffold polymer.

30. The method of embodiment 29, wherein the scaffold polymer is selected from the group consisting of poly (L-lactic acid) (PLLA), polycaprolactone (PCL), poly (lactic-co-glycolic acid) (PLGA), hydroxyapatite (HA), poly (lactide-co-ε-caprolactone) (PLCL), polytetrafluoroethylene (PTFE), expanded polytetrafluoroethylene (ePTFE), and combinations thereof.

31. The method of any one of embodiments 24-30, wherein the adhering of the coating polymer to the surface includes chemical vapor deposition (CVD).

32. The method of any one of embodiments 24-31, further comprising: activating the surface prior to the adhering of the coating polymer to the surface.

33. The method of embodiment 32, wherein the activating of the surface includes applying microwave plasma.

What is claimed is:

1. A scaffold sculpted or molded into a form of at least a portion of a stent, a shunt, a vascular graft, a patch, a cardiac valve, or a catheter, the scaffold comprising:
   a biopolymer functionalized with chemical groups facilitating covalent attachment of the biopolymer to a peptide ligand; and
   the peptide ligand, wherein the peptide ligand is covalently immobilized on the surface of the biopolymer, wherein the peptide ligand increases a number of endothelial cells and/or endothelial progenitor cells attached to the scaffold relative to a number of endothelial cells and/or endothelial progenitor cells attached to a corresponding scaffold not comprising the peptide ligand, and
   wherein the peptide ligand is cGRGDdvc (LXW7) (SEQ ID No. 1).

2. The scaffold of claim 1, wherein the biopolymer is selected from the group consisting of poly (L-lactic acid) (PLLA), polycaprolactone (PCL), poly (lactic-co-glycolic acid) (PLGA), poly(lactide-co-ε-caprolactone) (PLCL), polytetrafluoroethylene (PTFE), expanded polytetrafluoroethylene (ePTFE), and combinations thereof.

3. The scaffold of claim 1, wherein the biopolymer is a coating on at least a portion of a surface of the scaffold.

4. The scaffold of claim 3, wherein the coating is a parylene polymer.

5. The scaffold of claim 1, wherein endothelial cells, endothelial progenitor cells, and/or osteogenic cells are seeded on the scaffold.

6. The scaffold of claim 1, wherein the scaffold is an electrospun microfibrous scaffold.

7. The scaffold of claim 1, wherein the scaffold is a bony construct.

8. An engineered tissue comprising the scaffold of claim 1.

9. A coating on a surface of a scaffold sculpted or molded into a form of at least a portion of a stent, a shunt, a vascular graft, a patch, a cardiac valve, or a catheter comprising:
   a coating polymer; and
   the peptide ligand of claim 1, wherein the peptide ligand is covalently attached to the coating polymer.

10. The coating of claim 9, wherein the coating polymer is a parylene polymer.

11. A method for improving endothelialization and vascularization of endothelial cells and/or endothelial progenitor cells for tissue regeneration in a subject, the method comprising implanting the scaffold of claim 1 into the subject.

12. The method of claim 11, wherein the peptide ligand increases the recruitment of endothelial cells and/or endothelial progenitor cells to the scaffold.

13. The method of claim 11, wherein the peptide ligand increases the proliferation of endothelial cells and/or endothelial progenitor cells on the scaffold.

14. A method for repairing a bone defect in a subject, the method comprising implanting the scaffold of claim 1 into the subject.

15. The method of claim 14, wherein endothelial cells and osteogenic cells are seeded on the scaffold prior to implantation.

16. A method of coating a surface of a scaffold sculpted or molded into a form of at least a portion of a stent, a shunt, a vascular graft, a patch, a cardiac valve, or a catheter, the method comprising:
   functionalizing a coating biopolymer with chemical groups facilitating covalent attachment of the coating biopolymer to a peptide ligand;
   adhering the coating biopolymer to the surface; and
   covalently attaching the peptide ligand to the coating biopolymer, wherein the peptide ligand is the peptide ligand of claim 1 or a functionalized derivative thereof.

17. The method of claim 16, wherein the coating biopolymer is a parylene polymer.

18. The method of claim 16, wherein the functionalizing of the coating biopolymer includes introducing alkyne functional groups to the coating biopolymer.

19. The method of claim 18, wherein the peptide ligand is functionalized with an azide functional group.

20. The method of claim 16, wherein the scaffold comprises a scaffold polymer, a plastic, a metal, or a glass.

21. The method of claim 20, wherein the scaffold polymer is selected from the group consisting of poly (L-lactic acid) (PLLA), polycaprolactone (PCL), poly (lactic-co-glycolic acid) (PLGA), poly(lactide-co-ε-caprolactone) (PLCL), polytetrafluoroethylene (PTFE), expanded polytetrafluoroethylene (ePTFE), and combinations thereof.

22. The method of claim 16, wherein the adhering of the coating biopolymer to the surface includes chemical vapor deposition (CVD).

23. The method of claim 16, further comprising:
   activating the surface prior to the adhering of the coating biopolymer to the surface.

24. The method of claim 23, wherein the activating of the surface includes applying microwave plasma.

* * * * *